United States Patent
Blick et al.

(10) Patent No.: US 11,559,081 B2
(45) Date of Patent: Jan. 24, 2023

(54) AEROSOL PROVISION SYSTEM HAVING A BASE FOR SUPPORTING ONE OR MORE RECEPTACLES

(71) Applicant: BRITISH AMERICAN TOBACCO (INVESTMENTS) LIMITED, London (GB)

(72) Inventors: Kevin David Blick, London (GB); Alfred Vincent Spencer, London (GB); Julie Jenson Bennett, London (GB); Kelly Rees, London (GB); Connor Bruton, London (GB); Anna Koc, London (GB); Richard Hepworth, London (GB); Lisa Harvey, London (GB)

(73) Assignee: NICOVENTURES TRADING LIMITED, London (GB)

( * ) Notice: Subject to any disclaimer, the term of this patent is extended or adjusted under 35 U.S.C. 154(b) by 779 days.

(21) Appl. No.: 16/341,174

(22) PCT Filed: Oct. 5, 2017

(86) PCT No.: PCT/GB2017/053015
§ 371 (c)(1),
(2) Date: Apr. 11, 2019

(87) PCT Pub. No.: WO2018/069675
PCT Pub. Date: Apr. 19, 2018

(65) Prior Publication Data
US 2020/0178607 A1  Jun. 11, 2020

(30) Foreign Application Priority Data

Oct. 11, 2016 (GB) .................................. 1617244
Oct. 11, 2016 (GB) .................................. 1617245
Mar. 31, 2017 (GB) .................................. 1705204

(51) Int. Cl.
*A24F 40/46*  (2020.01)
*A24F 40/485* (2020.01)
(Continued)

(52) U.S. Cl.
CPC .................. *A24F 1/12* (2013.01); *A24F 7/00* (2013.01); *A24F 40/46* (2020.01); *A24F 40/485* (2020.01);
(Continued)

(58) Field of Classification Search
CPC ........ A24F 40/485; A24F 40/46; A24F 40/40; A24F 1/30
See application file for complete search history.

(56) References Cited

U.S. PATENT DOCUMENTS

| | | |
|---|---|---|
| 4,133,318 A | 1/1979 | Gross |
| 6,234,167 B1 | 5/2001 | Cox et al. |

(Continued)

FOREIGN PATENT DOCUMENTS

| | | |
|---|---|---|
| CN | 205512358 U | 8/2016 |
| CN | 105962421 A | 9/2016 |

(Continued)

OTHER PUBLICATIONS

International Search Report and Written Opinion, Application No. PCT/GB2017/053015, dated Mar. 6, 2018, 17 pages.
(Continued)

*Primary Examiner* — Hae Moon Hyeon
(74) *Attorney, Agent, or Firm* — Patterson Thuente, P.A

(57) ABSTRACT

An aerosol provision system includes one or more receptacles each forming a respective central space, a base adapted to support the or each receptacle, the or each receptacle being removable from the base and at least a first airflow generator, operable to draw air through at least a first aerosol generator, wherein the base includes one or more
(Continued)

outlets through which, in operation, aerosolized payload is directed to flow from the base into the central space of a respective receptacle and the or each receptacle comprises a first opening through which the user can inhale the aerosolized payload.

20 Claims, 13 Drawing Sheets

(51) Int. Cl.
| | | |
|---|---|---|
| A24F 1/12 | (2006.01) | |
| A61M 15/00 | (2006.01) | |
| A61M 11/00 | (2006.01) | |
| A61M 15/06 | (2006.01) | |
| A61M 11/04 | (2006.01) | |
| A24F 40/51 | (2020.01) | |
| A24F 7/00 | (2006.01) | |
| A61M 21/00 | (2006.01) | |
| A61M 15/02 | (2006.01) | |
| A24F 40/50 | (2020.01) | |
| A24F 40/10 | (2020.01) | |

(52) U.S. Cl.
CPC .......... *A24F 40/51* (2020.01); *A61M 11/005* (2013.01); *A61M 11/042* (2014.02); *A61M 15/0065* (2013.01); *A61M 15/0086* (2013.01); *A61M 15/06* (2013.01); *A24F 40/10* (2020.01); *A24F 40/50* (2020.01); *A61M 15/0016* (2014.02); *A61M 15/0021* (2014.02); *A61M 15/02* (2013.01); *A61M 2021/0044* (2013.01); *A61M 2205/07* (2013.01); *A61M 2205/075* (2013.01); *A61M 2205/13* (2013.01); *A61M 2205/14* (2013.01); *A61M 2205/18* (2013.01); *A61M 2205/332* (2013.01); *A61M 2205/3306* (2013.01); *A61M 2205/587* (2013.01); *A61M 2205/59* (2013.01); *A61M 2205/8206* (2013.01); *A61M 2205/8262* (2013.01); *A61M 2209/084* (2013.01)

(56) References Cited

U.S. PATENT DOCUMENTS

| | | | |
|---|---|---|---|
| 6,513,524 B1 | 2/2003 | Storz | |
| 6,708,572 B2 | 3/2004 | Jenkins et al. | |
| 6,923,179 B2 | 8/2005 | Gupta et al. | |
| 8,490,629 B1 * | 7/2013 | Shenassa | A24F 1/28 131/198.2 |
| 2003/0056789 A1 | 3/2003 | Takano | |
| 2004/0129793 A1 | 7/2004 | Nguyen | |
| 2008/0029107 A1 * | 2/2008 | Ruff | A24F 1/30 131/173 |
| 2009/0013993 A1 | 1/2009 | Bird et al. | |
| 2011/0049266 A1 | 3/2011 | Jorgensen | |
| 2011/0051983 A1 | 3/2011 | Jorgensen | |
| 2011/0308521 A1 | 12/2011 | Kofford | |
| 2012/0199572 A1 | 8/2012 | Shen | |
| 2013/0074857 A1 | 3/2013 | Buchberger | |
| 2014/0130812 A1 | 5/2014 | Kling et al. | |
| 2014/0144429 A1 | 5/2014 | Wensley | |
| 2014/0291414 A1 * | 10/2014 | Bretillot | B05B 17/0615 239/68 |
| 2015/0196060 A1 | 7/2015 | Wensley | |
| 2015/0305409 A1 | 10/2015 | Verleur et al. | |
| 2015/0374935 A1 | 12/2015 | Bouchard | |
| 2016/0278435 A1 | 9/2016 | Choukroun et al. | |
| 2016/0331913 A1 | 11/2016 | Bourque | |
| 2017/0259170 A1 | 9/2017 | Bowen et al. | |
| 2018/0056015 A1 * | 3/2018 | Shwadchuck | A61M 15/0086 |
| 2019/0099562 A1 | 4/2019 | Nettenstrom et al. | |
| 2019/0230992 A1 | 8/2019 | Blick et al. | |

FOREIGN PATENT DOCUMENTS

| | | |
|---|---|---|
| FR | 3018463 | 9/2015 |
| RU | 2131750 C1 | 6/1999 |
| RU | 2232032 C2 | 7/2004 |
| RU | 125029 U1 | 2/2013 |
| RU | 130798 U1 | 8/2013 |
| WO | WO-03026556 A2 | 4/2003 |
| WO | WO14183073 | 11/2014 |
| WO | WO2015116934 | 8/2015 |
| WO | WO2016066677 | 5/2016 |

OTHER PUBLICATIONS

Great Britain Search Report, Application No. GB 1617245.4, dated Feb. 24, 2017, 3 pages.
International Preliminary Report on Patentability, Application No. PCT/GB2017/053015, dated Jan. 29, 2019, 12 pages.
Partial International Search Report, Application No. PCT/GB2017/053015, dated Jan. 8, 2018, 12 pages.
Decision of Grant dated Nov. 27, 2019 and Search report for Russian Patent Application No. 2019110650, 13 pages.
International Preliminary Reporton Patentability for Application No. PCT/GB2017/053017, dated Jan. 4, 2019, 10 pages.
International Search Report and Written Opinion for Application No. PCT/GB2017/053017, dated Mar. 6, 2018, 15 pages.
Office Action dated Jun. 30, 2020 for Russian Application No. 2019110647, 6 pages.
Partial International Search Report for Application No. PCT/GB2017/053017, dated Jan. 8, 2018, 9 pages.
Search report dated Mar. 16, 2020 for Russian Application No. 2019110647, 2 pages.
Search Report dated Feb. 24, 2017 for Great Britain Application No. GB1617244.7, 4 pages.

* cited by examiner

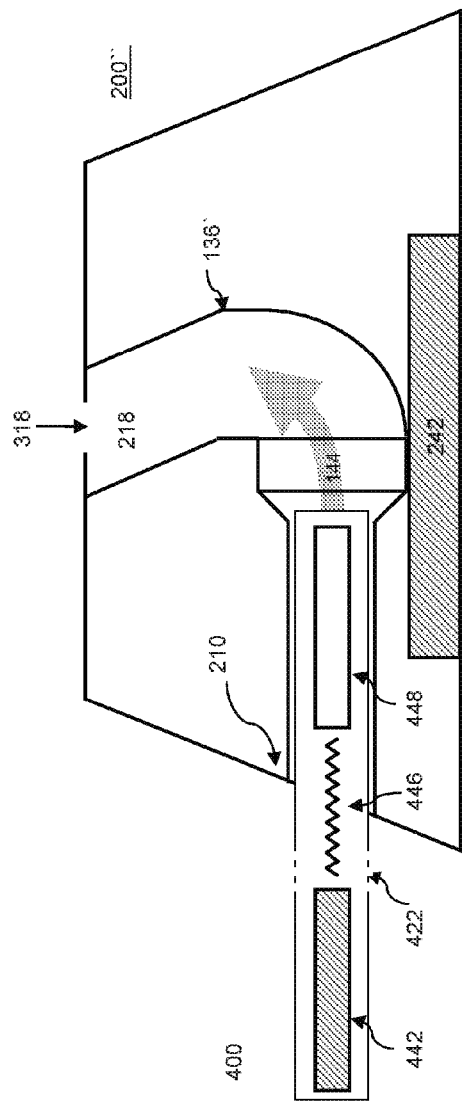

```
┌─────────────────────────────────────────────────────┐
│ Provide one or more receptacles each forming a       │ s111
│ respective partially enclosed central space          │
└─────────────────────────────────────────────────────┘
                          ↓
┌─────────────────────────────────────────────────────┐
│ Provide a base adapted to support the or each        │ s112
│ receptacle, the or each receptacle being removable   │
│ from the base                                        │
└─────────────────────────────────────────────────────┘
                          ↓
┌─────────────────────────────────────────────────────┐
│ Provide a plurality of respective aerosol generators │ s113
│ operable to generate said aerosolised payload for at │
│ least a respective one of the receptacles            │
└─────────────────────────────────────────────────────┘
                          ↓
┌─────────────────────────────────────────────────────┐
│ Provide at least a first airflow generator, operable │ s114
│ to draw air through the aerosol generators           │
└─────────────────────────────────────────────────────┘
                          ↓
┌─────────────────────────────────────────────────────┐
│ Direct aerosolised payloads to flow from the base    │ s115
│ through a lower opening of a respective receptacle   │
│ into the respective central space of the or each     │
│ supported receptacle through respective outlets of   │
│ the base                                             │
└─────────────────────────────────────────────────────┘
```

*Figure 14*

AEROSOL PROVISION SYSTEM HAVING A BASE FOR SUPPORTING ONE OR MORE RECEPTACLES

PRIORITY CLAIM

The present application is a National Phase entry of PCT Application No. PCT/GB2017/053015, filed Oct. 5, 2017, which claims priority from GB Patent Application No. 1617245.4, filed Oct. 11, 2016, GB Patent Application No. 1617244.7, filed Oct. 11, 2016 and GB Patent Application No. 1705204.4, filed Mar. 31, 2017, each of which is hereby fully incorporated herein by reference.

FIELD

The present disclosure relates to an aerosol provision system and method.

BACKGROUND

Aerosol provision (AP) systems, such as e-cigarettes, non-combustion tobacco heating systems and other aerosol delivery systems, generally hold a payload/substrate that is either a reservoir of liquid which is to be vaporized, typically comprising nicotine (this is sometimes referred to as an "e-liquid"), or a reservoir of plant material or some other (ostensibly solid) plant derivative or material from which volatiles or other liquids or particulate solids may be liberated. When a user inhales on the device, an electrical (e.g. resistive) heater is activated to vaporize a small amount of liquid or release volatiles, particulates etc., in effect producing an aerosol which is consequently inhaled by the user. The liquid may comprise nicotine in a solvent, such as ethanol or water, together with glycerine or propylene glycol to aid aerosol formation, and may also include one or more additional flavors. The plant material may comprise tobacco or a derivative. The skilled person will be aware of many different payload formulations that may be used in AP systems.

The practice of inhaling an aerosol in this manner is commonly known as 'vaping'.

However, such AP systems are typically viewed as individual and personal items that it would be unhygienic to share with others, limiting the sociability of their use, and also potentially dissuading users from experiencing different payload flavors that they may otherwise enjoy.

SUMMARY

The present disclosure seeks to address or mitigate this problem.

In a first aspect, an aerosol provision (AP) system is provided in accordance with claim 1.

In another aspect, a hand-held receptacle for holding aerosolized payload is provided in accordance with claim 15.

In another aspect, a base unit for an aerosol provision system is provided in accordance with claim 19.

In another aspect, a method of an aerosol provision is provided in accordance with claim 22.

Further respective aspects and features of the disclosure are defined in the appended claims.

BRIEF DESCRIPTION OF THE DRAWINGS

Embodiments of the present disclosure will now be described by way of example with reference to the accompanying drawings, in which like reference numerals designate identical or corresponding parts throughout the several views:

FIG. 8 is a schematic diagram of a base of an AP system in accordance with an embodiment of the present disclosure.

FIG. 14 is a flow diagram of a method of aerosol provision in accordance with an embodiment of the present disclosure.

DETAILED DESCRIPTION

An aerosol provision system and method are disclosed. In the following description, a number of specific details are presented in order to provide a thorough understanding of the embodiments of the present disclosure. It will be apparent, however, to a person skilled in the art that these specific details need not be employed to practice the present disclosure. Conversely, specific details known to the person skilled in the art are omitted for the purposes of clarity where appropriate.

As was noted previously herein, conventional AP systems such as e-cigarettes require the user to put the system in their mouth; this allows the user to draw in air and create an airflow through the device. Typically this airflow is detected and used to trigger heating of the liquid or solid payload to create an airborne payload (i.e. vapor, volatiles and/or particulates), which is then caught in the airflow to form an aerosolized payload that is inhaled by the user, although alternatively the device can be triggered via a button pressed substantially simultaneously to inhalation. It will be understood that where the description refers to 'liquid' or 'e-liquid' it encompasses equivalent solid plant matter sources, and similarly 'vapor encompasses equivalent volatiles and particulates (i.e. those contributing to an aerosolized payload for inhalation) unless explicitly stated.

Hence in such conventional systems, inhalation by the user is important to detect when to activate the system and to provide the airflow necessary to transport aerosolized payload to the user. However this requires that the aerosol provision system is held in the user's mouth sufficiently tightly that inhalation causes sufficient air to flow through the AP system.

As a result, it may be considered unhygienic to share an AP system between several users, and particularly between acquaintances and relative strangers such as may be encountered at a dinner party or other casual social gathering. This limits the scope for a communal experience and for sharing or trying out liquids and flavors enjoyed by others in the group.

Figure 1:
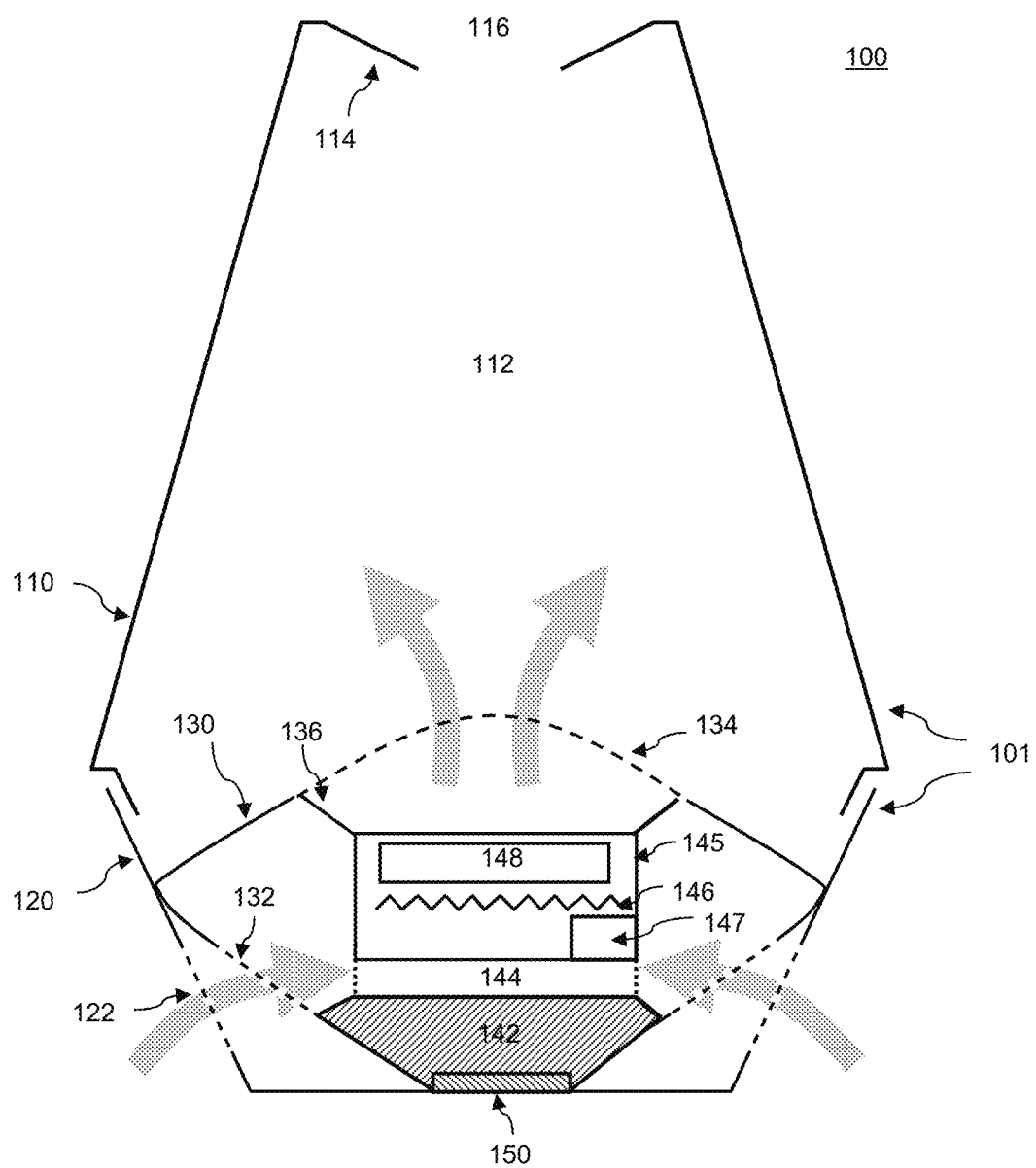
FIG. 1 is a schematic diagram of an AP system in accordance with an embodiment of the present disclosure.

Accordingly, and referring now to FIG. 1, in an embodiment of the present disclosure an AP system 100 is arranged in operation to generate its own airflow.

Figure 2:
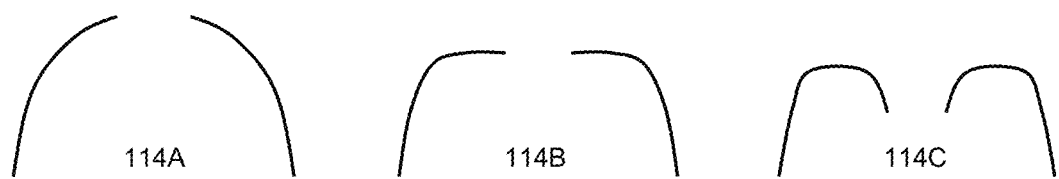
FIG. 2 is a schematic diagram of representative lip shapes of a receptacle of an AP system in accordance with an embodiment of the present disclosure.

The illustrated AP system resembles a handheld drinking glass or tumbler such as a whiskey glass or tulip-shaped bowl, although the particular appearance or material is not essential; more generally the AP system comprises a receptacle 101 arranged to house an aerosol generator and provide a central volume 112 (which can be partially enclosed) within which the vapor may collect. Optionally the receptacle may have a lip 114 that serves to decrease the radius of an upper opening at the top of the receptacle. Referring to FIG. 2, optionally the lip may take the form of a tapering of the walls to form an egg-like shape as per lip 114A, or may be substantially horizontal as per lip 114B, or may point or curve downwards in the center as per lip 114C and lip 114 in FIG. 1. By pointing or curving downwards, the lip can cause vapor flowing up the inside of the receptacle walls to be diverted back into the central volume 112 of the receptacle.

In this embodiment, the receptacle 101 is separable into two parts 110, 120 to facilitate cleaning and also to provide access to the aerosol generator 130.

The lower part 120 of the receptacle 101 comprises one or more air vents 122 to allow a flow of air into the lower part of the receptacle. Similarly one or more air vents 132 in a lower part of the aerosol generator enable a flow of this air into the aerosol generator.

The aerosol generator in turn comprises a battery 142, and an airflow generator 144 (for example a so-called microblower such as a piezo blower, or alternatively a motorized fan or pump; alternatively a compressed air or gas source (e.g. $CO_2$) with an electrically actuated release may be used, but is not shown in the Figures). In operation, a blower, pump or fan draws air in through the air vents 122 and directs it to an atomizer 145 which includes the payload 148, e.g. a reservoir of liquid or solid material as described previously herein, and a heater 146. It will be appreciated that in the case where compressed air/gas is used, then air vents may not be required in the lower part of the receptacle or aerosol generator. It will also be appreciated that the aerosol may be formed without using a heater, such as via the use of piezo-electric vibration, or other mechanical means. It is also possible to create aerosols via electro-static atomization, and the use of such in the present atomizer is explicitly contemplated. Hence the atomizer may employ any one or more of the above mechanisms to generate an aerosol, and references herein to a heater 146 incorporate these alternatives as applicable.

The atomizer 145 operates in a similar manner to conventional AP systems, and may generate vapor in any suitable manner. For example, the payload 148 in the atomizer may hold an e-liquid directly in liquid form, or may utilize some absorbing structure, such as a foam matrix or cotton material, etc, as a retainer for the liquid.

The liquid is then fed from the payload 148 to the heater 146 for atomization (e.g. by vaporization) to form an airborne payload. For example, the liquid may flow via capillary action from the payload 148 to the heater 146 via a wick (not shown in FIG. 1). The air flow generated from the pump or air blower then combines with the airborne payload to form an aerosol, which then flows out of the atomizer.

In other instances, as noted previously herein the liquid (or equivalently volatiles or particulates) may be provided in the form of plant material or some other (ostensibly solid) plant derivative or material, typically but not necessarily based on tobacco, or any suitable botanical. In this case the liquid can be considered as representing volatiles or particulates in the material which vaporize when the material is heated without combustion. Note that AP systems containing this type of material generally do not require a wick to transport the liquid to the heater, but rather provide a suitable arrangement of the heater in relation to the material to provide suitable heating.

Alternatively the payload may be a gel or a combination such as a botanical product impregnated with a liquid, or a botanical product in a liquid or gel suspension. Similarly in principle the payload may be a botanical product, gel product and/or liquid product that are each separately vaporized within the device, potentially to varying degrees, with their respective vapors being combined and blended within the airflow. It will be appreciated that the active ingredient or ingredients within the payload may be variously soporific, neutral or stimulating as desired.

Hence an aerosol may be generated for example by heating (but not combusting) tobacco. However purely for the purposes of explanation, and without limitation, the description herein refers to the payload as liquid where specified.

The aerosol may then flow through an optional covering 134. If necessary, flow guides 136 may be provided to ensure that the aerosol passes out of the aerosol generator rather than accumulating to any significant extent within the body of the aerosol generator itself. The optional covering comprises vents to enable the aerosol vapor to pass into the central volume 112 of the AP system.

Typically the optional covering will be removable to enable access to the payload 148, which may take the form of a removable cartridge that can be replaced or interchanged with different cartridges to provide different flavors or strengths of vapor. Again, such a cartridge may operate in a similar manner to cartridges in conventional AP systems.

Alternatively, the payload may be inaccessible to the user; for example the aerosol generator may be a sealed, disposable unit.

The aerosol generator also comprises a control unit (not shown in FIG. 1) and also optionally a sensor 150, discussed later herein.

Figure 3:
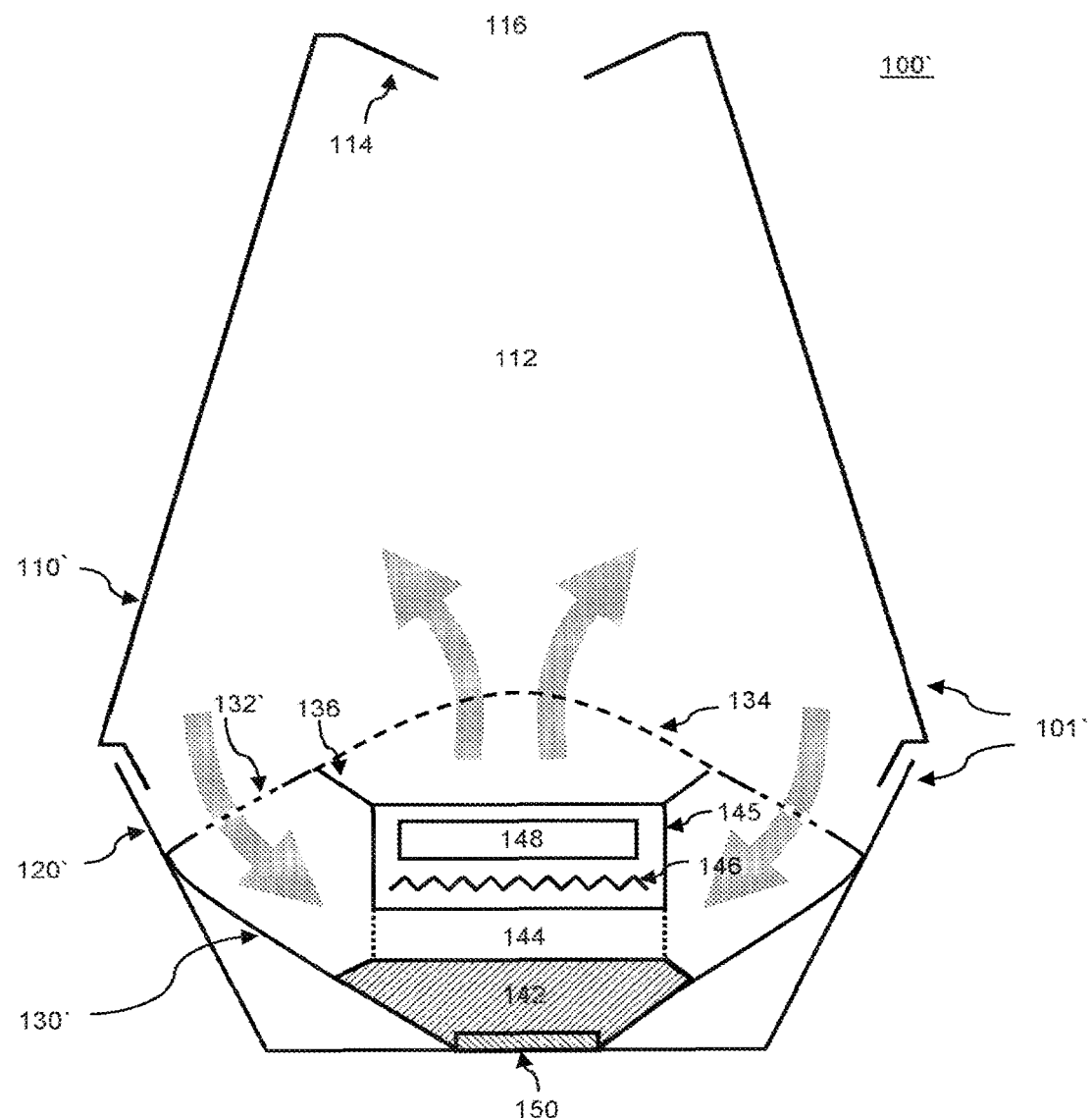
FIG. 3 is a schematic diagram of an AP system in accordance with an embodiment of the present disclosure.

In the example above, where a pump, fan or blower is used, air is drawn into a lower part 120 of the receptacle 101 and passed upwards through the atomizer 145 into the central volume 112 of the receptacle 101. However, referring now to FIG. 3, alternatively in an AP system 100', the lower part 120' of the receptacle 101' and of the aerosol generator 130' may not comprise air vents, and instead during operation air may be drawn through the upper opening 116 of the receptacle and through upper vents 132' in a first region of the upper surface of the aerosol generator 130' before being recirculated through one or more vents 134 in a second region of the upper surface of the aerosol generator. For example, as illustrated in FIG. 3 air may be drawn in through a peripheral or circumferential set of upper vents 132' in the upper surface of the aerosol generator, before passing the aerosol out through a central region 134, in a similar manner to the output of an aerosol in FIG. 1. Alternatively the air may be drawn centrally down from the opening in the receptacle to a central region of the upper surface of the aerosol generator, before passing the aerosol out through peripheral or circumferential vents or perforations into the central volume 112 near the inside walls of the receptacle.

This may advantageously cause an internal circulation of air within the central region of the receptacle that causes an even distribution of aerosolized payload within the receptacle. However, problematically it may cause some of any existing vapor within the central region of the receptacle to be drawn into the pump, which over the course of repeated operations may impair the pump's performance. This effect can however be mitigated by suitable control of the AP system, as described later herein.

Figure 4A:
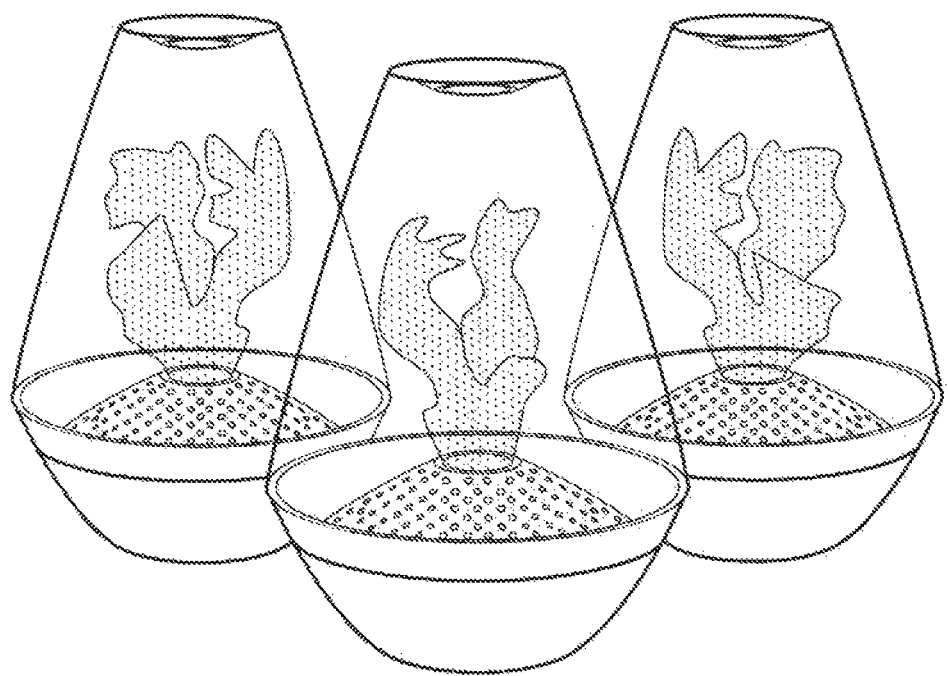
FIGS. 4A and 4B are illustrative examples of an AP system in accordance with an embodiment of the present disclosure.
Figure 4B:
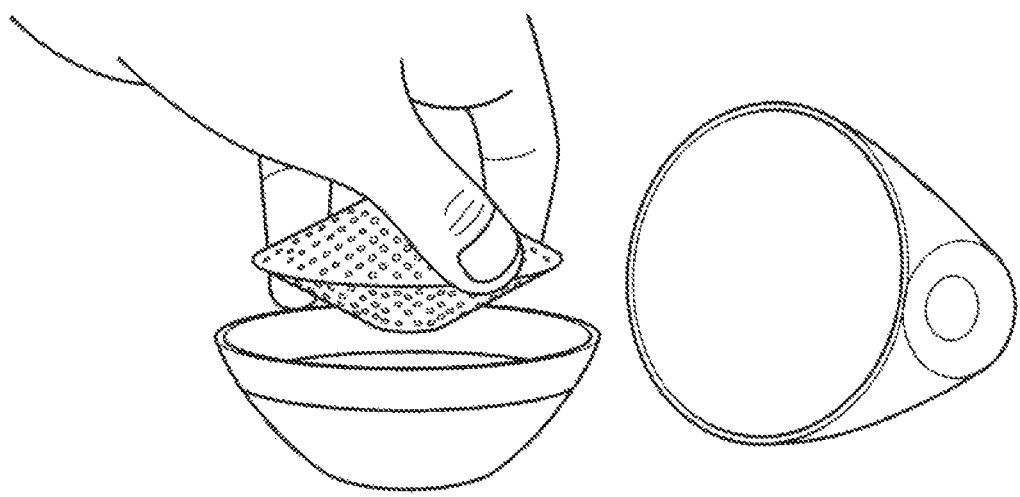

Exemplary illustrations of the AP system in operation and disassembled for cleaning/cartridge replacement are shown in FIGS. 4A and 4B respectively.

Thus more generally, the arrangements of FIG. 1 and FIG. 3 provide a receptacle 101, 101' for an e-liquid aerosol generated by an aerosol generator within the receptacle, which in turn comprises an electrically powered air flow source such as an air blower operable to draw air into the receptacle (or in the case of compressed air/gas release it into the receptacle) and through a atomizer that heats the liquid to generate a vapor; the vapor in turn mixes with the drawn air to form the aerosol which then flows out of the vapor generator and into the partially enclosed central volume of the receptacle.

In this way, the device can provide a contained bolus of aerosolized payload (such as vapor, volatiles, and/or particulates) that can be inhaled by a user when they pick up the receptacle and inhale the vapor through their mouth or nose near the upper opening 116 of the receptacle, thereby drawing the aerosol out of the receptacle to the user.

Notably therefore the user does not have to place the receptacle in their mouth, and furthermore the AP system is not dependent upon an inhalation by the user to generate a dose of aerosolized payload within the brief but variable period of time afforded by that action. However, it is not excluded that the user's mouth may contact the receptacle during use, and it may be that the receptacle allows for the produced vapor to be "sipped" in a manner similar to the sipping of drink from a tumbler.

Given that the AP systems of FIGS. 1 and 3 do not depend upon detecting inhalation to generate aerosolized payload, an alternative control mechanism for generating aerosolized payload is required.

In an embodiment of the present disclosure, the AP system optionally comprises a sensor 150 to detect an interaction with the receptacle by a user. The sensor may be a tilt switch, accelerometer or gyroscope to detect physical movement of the receptacle. Alternatively or in addition the sensor may be a photoresistor located on the base of the receptacle to electronically detect light when the receptacle is lifted up. In order to improve battery life, an electrically passive detector may be provided such as a photocell which generates electricity in response to the detection of light. In this case, the electronics of the aerosol generator may be off until a small voltage from the photocell triggers activation of the device, for example by supplying a small voltage to the gate of a transistor connected to the power supply, thereby allowing detected light to reactivate the aerosol generator. Alternatively or in addition, the sensor may be a physical switch in the base of the receptacle, such as a push switch that is in the off position when depressed; as a result the AP system would be off when the receptacle is placed on a surface, but would turn on when picked up. Other sensor mechanisms will be apparent to the skilled person, such as capacitance detection, allowing detection of touch of the receptacle by a user.

In any event, when an interaction with the user is detected by a sensor or sensors, the aerosol generator 130, 130' activates to generate aerosolized payload in the manner described previously, namely by activating the electrically powered micro-blower, fan, pump or pressurized air source 144 to draw or introduce air into the atomizer 145 where it mixes with airborne payload to form an aerosol that is introduced into the partially enclosed central space of the receptacle.

After a predetermined time period that may be determined empirically to adequately fill the receptacle with aerosolized payload, the aerosol generator stops.

In this way, the receptacle 101, 101' fills with the bolus of aerosolized payload as the user picks the receptacle up to inhale from it.

Alternatively or in addition, in an embodiment of the present disclosure the aerosol generator may produce aerosolized payload periodically. This may serve to ensure that a bolus of aerosolized payload is available within the receptacle in the case where either there is no sensor provided, or the sensor is unable to detect interaction with the user (for example, if the user is in an environment with low lighting, it is possible that a photoresistor, photodiode or photocell may not detect an adequate change in brightness when the AP system is picked up).

Furthermore, where at least the upper part 110 of the receptacle is glass or some other transparent material, a periodic production of aerosolized payload will ensure an attractive cloud is visibly present within the receptacle, and may also remind the user either of the option to inhale the aerosolized payload, or at least that the device is on and may need to be switched off.

In this embodiment, the periodicity of aerosolized payload production is controlled by a control unit (not shown) and may at least initially be predetermined. The periodicity may also be set depending upon factors such as the size of the receptacle, the type of liquid in the reservoir, the ambient temperature, and how often the AP system detects that it is being picked up and used, if a sensor such as one of those described above is included.

The vapor generator may optionally also include one or more lights, such as for example a warm white light emitting diode (LED). If positioned underneath the vents or perforations in the upper surface of the aerosol generator, the each light can provide a pleasing tea-light or candle-like ambient lighting.

When the AP system is arranged to periodically produce aerosolized payload, optionally the control unit may control the light so that it changes during the aerosolized payload generation period, for example by turning on, changing intensity (either brighter or dimmer), or changing color.

When the AP system is picked up, the light may stay on, or if it is equipped with a sensor such as one of those described above, optionally it may dim or turn off so as to not strongly illuminate the user's face from below while they inhale from the receptacle.

Hence also in the case where the the AP system also generates aerosolized payload in response to being picked up, any light may change intensity or color during the aerosolized payload generation period as described above in relation to the periodic production of aerosolized payload, but then quickly thereafter dim or turn off as the receptacle is brought closer to the user's face; alternatively any light may dim or turn off when the receptacle is picked up, and not change in response to aerosolized payload being generated.

Furthermore, whether periodically generated or generated in response to user interaction, the control unit may set a predetermined time period for aerosolized payload generation. This time period may for example correspond to the period of time required by the blower/pump/fan to draw a certain volume of air into the receptacle, or for a compressed air source to release an equivalent volume of air, where that volume is for example a predetermined percentage of the volume of air in the upper part of the receptacle. For example, an amount of equivalent to 10, 20, 30, 40, 50, 60, 70, 80, 90, or 100% of the volume of air may be predetermined, and the time period set accordingly.

Referring particularly to the embodiment illustrated in FIG. 3, the percentage of the volume of air may be selected to reduce the chances that a significant amount of aerosolized payload already in the partially enclosed central volume of the receptacle re-enters the aerosol generator. For example, it may be assumed that the air in the region surrounding the periphery of the aerosol generator comprises a relatively low proportion of aerosolized payload, so that generating smaller puffs of aerosolized payload more regularly only introduces air from a small proportion of the receptacle near to the outer vents. The precise proportion of air will depend upon the design of the receptacle and the upper surface of the aerosol generator.

Notably, because the device is not activated by airflow, the heater 146 can optionally be preheated prior to activation of airflow where this is beneficial to the atomization process, so that airborne payload starts be generated just as the airflow begins. This helps to provide a consistent and repeatable volume of aerosolized payload with each activation of the aerosol generator.

Furthermore, the rate of airflow may optionally be controlled by the control unit through electrical control of the blower/pump/fan or compressed air/gas source; this can be used to control the size of aerosol particles that are formed as the airborne payload mixes with the air flow. The air flow rate may vary for example depending upon the selection of e-liquid that is being vaporized. In this case, clearly the predetermined time period may vary as a function of the airflow rate to introduce the same overall intended volume of air.

Optionally, the receptacle itself may be warmed, either by conduction using a heater in aerosol generator, or by use of resistive film on the receptacle, which may be powered by electrical contacts on the aerosol generator. The warming of the receptacle may be provided to reduce the chance of aerosolized payload condensing on the inside walls of the receptacle. Optionally this may be controlled by a thermistor or other temperature sensor. Alternatively or in addition, a light (such as described above) may be used to indicate a low ambient temperature. Hence for example, the light may appear blue if a threshold temperature is detected where condensation within the receptacle is likely. Alternatively or in addition, in response to the ambient threshold being below a threshold, the airflow generator may be activated without corresponding activation of the atomizer to stir air within the receptacle and remove condensation, or if it is already operating periodically, the frequency may be increased.

It will be appreciated that the battery 142 may be replaceable, and/or rechargeable. In the case where it is rechargeable, the aerosol generator may have a charging port, or may be supplied with a corresponding charging dock onto which may be placed. Charging may be by induction, potentially enabling charging of the aerosol generator whilst it is still located in its operating position within the receptacle.

Alternatively or in addition, charging may be via contacts accessible on the outside of the aerosol generator that are brought into contact with pins or the like on the charging dock. Optionally, where air vents are incorporated into the lower part of the AP system, such contacts may be accessible for charging purposes via such vents while the aerosol generator is still located in its operating position within the receptacle.

The preceding embodiments assume that the AP system is self-contained during operation, even if a charging dock is provided. However, referring now to FIG. 5, in an embodiment of the disclosure the AP system 100" does not contain a battery, thereby potentially reducing the size of the aerosol generator 130" and also reducing the weight of the AP system itself.

Instead, a base (200) is provided, which may optionally contain a battery (242) which in turn may be of greater capacity than might otherwise be provided within the aerosol generator due to weight/size considerations. Alternatively or in addition, an external power supply maybe connected to the base to charge the battery and/or provide power together with or in lieu of the battery to the aerosol generator. The base comprises an upper supporting surface 201 that provides a receiving space for the receptacle (101, 101'). This may simply be a flat surface, or an indented or dished/concave region of corresponding shape to the receptacle.

In a case where the AP system only generates aerosolized payload periodically, the base can be connected to the aerosol generator to provide power directly, without any local power source being included within the aerosol generator. Furthermore, the control unit may also be located in the base to control the supply of power for predetermined time periods, as described previously herein.

Alternatively or in addition, where the AP system generates aerosolized payload in response to user interaction such as being picked up off the base, a temporary power source 152 may be required to drive sufficient air and generate a sufficient heat to release one bolus of aerosolized payload into the receptacle. An example temporary power source may be a suitably sized capacitor. In this case, the control unit may still be in the base, and the capacitor discharges to drive the aerosol generator in response to being electrically decoupled from the base. Alternatively the control unit (or a secondary control unit) may be located in the aerosol generator to control power use.

It will be appreciated that the example of one bolus above is non-limiting, and temporary power for two or more uses may be considered, subject to the size and weight of capacitor selected for inclusion in the aerosol generator. This would allow the AP system to be passed around several people before being returned to the base. In this case, the control unit or secondary control unit may be located in the aerosol generator to control aerosol generation in a manner similar to that described previously in relation to FIGS. 1 and 3.

Figure 5:
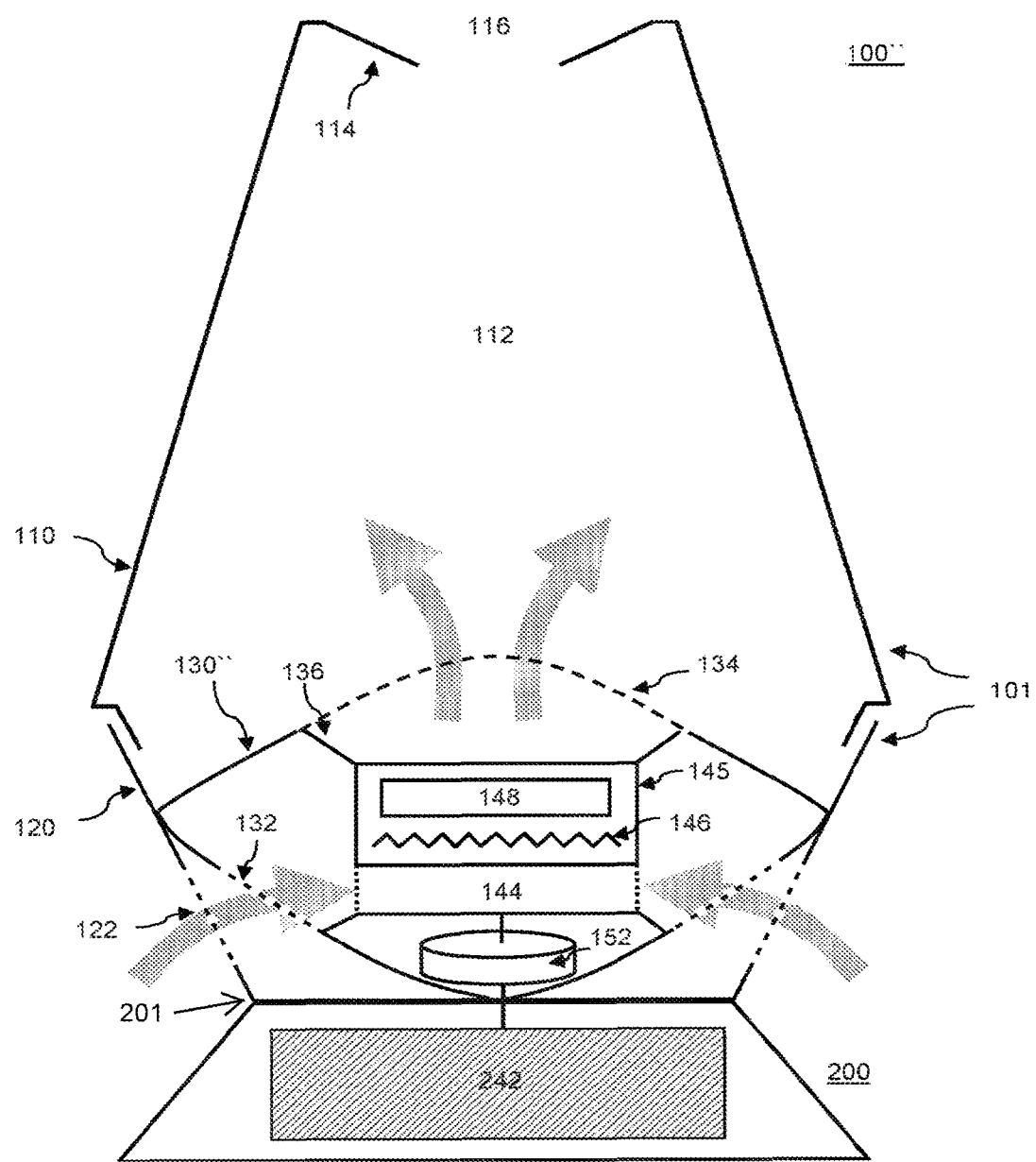
FIG. 5 is a schematic diagram of an AP system in accordance with an embodiment of the present disclosure.

It will be appreciated that the AP system 100" shown in FIG. 5 has the air flow arrangement shown in FIG. 1, but of course equally it may have the air flow arrangement shown in FIG. 3, or indeed any other suitable air flow arrangement, such as for example via the base and up through vents on the underside of the receptacle (not shown). In this case, it would leave the walls of the lower part of the receptacle continuous, potentially making the receptacle more comfortable to hold.

It will be appreciated that the arrangement of components in FIGS. 1, 3 and 5 is purely illustrative and non-limiting, and that any suitable arrangement may be considered, such as for example in the case of FIGS. 1 and 3 the battery being a separate unit located in the base of the receptacle and/or in the case of any of these three figures, the pump, fan or blower being located downstream of the atomizer and arranged to draw air through the atomizer rather than blow air through the atomizer.

In any one of the embodiments of FIGS. 1, 3 and 5, optionally the airflow generator 144 (the pump, fan or blower) may be activated on its own (i.e. without a corresponding activation of the atomizer to generate aerosolized payload). This may be done to blow existing aerosolized payload held in the receptacle out through the opening 116. This may be done periodically to at least partially vacate the central volume 112 in order to allow fresher aerosolized payload to be introduced into the receptacle.

Alternatively or in addition, it may be done upon detection that the receptacle has been picked up (optionally after a small delay in the order of tenths of seconds, or after detection of the receptacle being tipped, as if being held towards a user's nose), in order to direct the aerosolized payload within the partially enclosed central region out through the opening 116. This further assists the user in inhaling the aerosolized payload without having to come into close contact with the receptacle, and without having to touch it with their lips or nose, or place part of it within their mouths.

Figure 6:
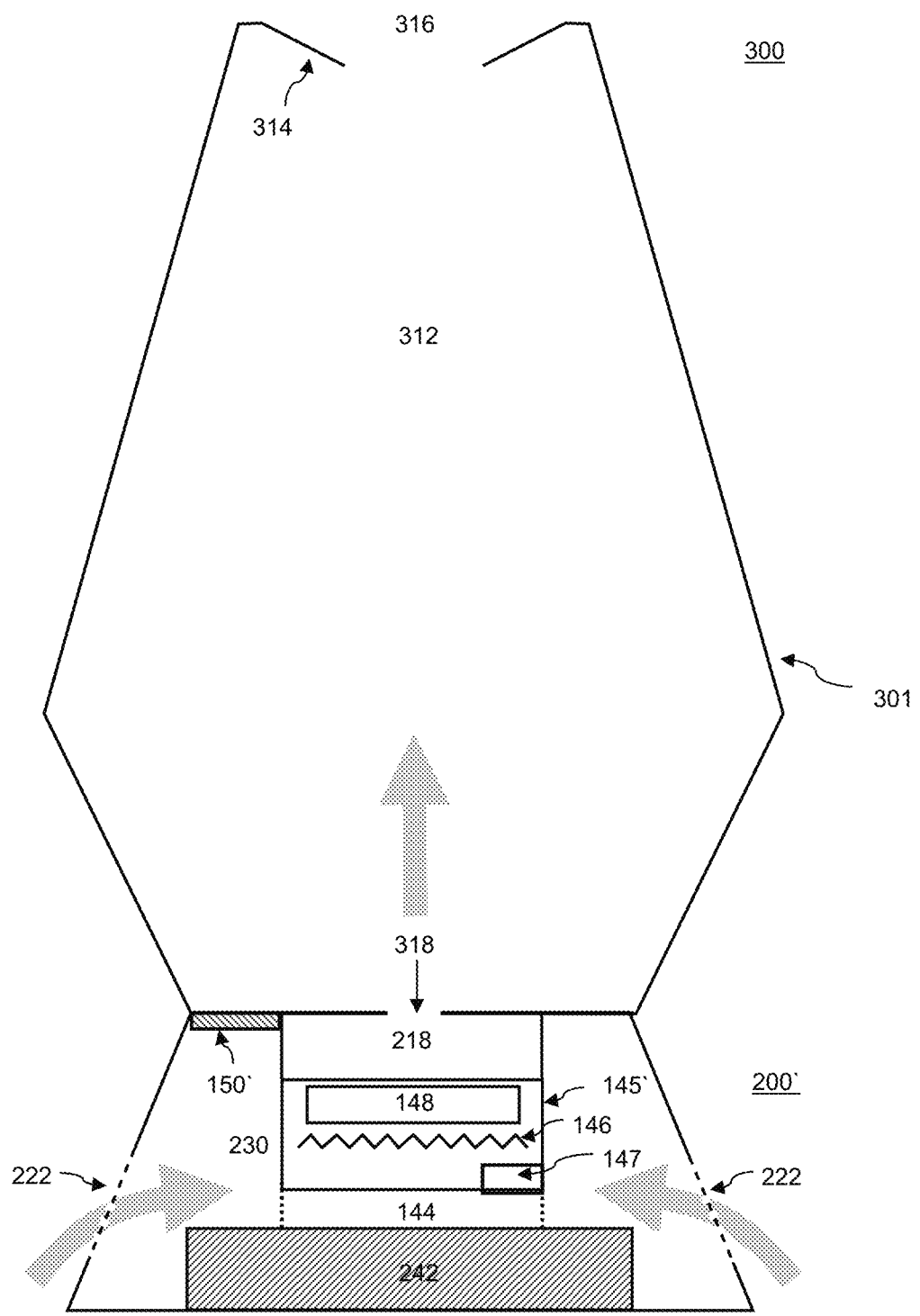
FIG. 6 is a schematic diagram of an AP system in accordance with an embodiment of the present disclosure.

Turning now to FIG. 6, in an embodiment of the present disclosure, in an AP system 300 the aerosol generator 230 is also incorporated into the base 200'.

As a result, the receptacle 301 may no longer need to be made of separable parts to provide access to an internally positioned aerosol generator. The overall shape of the receptacle may remain the same as in previous embodiments, or may adopt alternate decorative designs that are no longer constrained by the need to incorporate the aerosol generator. However in general they will still comprise a partially enclosed central volume 312 and an upper opening 316 through which a user may inhale aerosolized payload. Also as in the previous embodiments, the receptacle may comprise a lip 314 of any suitable design, as described previously herein.

Moreover, the receptacle no longer needs air vents in the lower portion of the receptacle, allowing for the walls of the receptacle to be continuous. This may be more comfortable for a user to hold. Instead, where airflow is provided by a blower, pump or fan in the base, the air vents 222 are also located in the base to allow the air to be drawn in.

In addition, the receptacle 301 comprises a lower opening 318 through which aerosolized payload is introduced into the partially enclosed central volume. Typically the effective area of the lower opening will be smaller than that of the upper opening. For example the diameter of the upper opening may be in the order of centimeters, whilst the diameter of the lower opening may be in the order of millimeters. More generally therefore the upper opening is larger than the lower opening 318.

By way of a non-limiting example, the diameter of the upper opening may be one, two, three, four, five, six, seven, eight, nine, or ten centimeters in diameter, whilst the diameter of the lower opening 318 may be one, two, three, four, five, six, seven, eight, nine, or ten millimeters in diameter. It will be appreciated however that other diameters may be selected where appropriate.

More generally, as a non-limiting example the ratio of the diameters of the upper and lower openings may be 1.5:1, 2:1, 2.5:1, 3:1, 4:1, 5:1, 6:1, 7:1, 8:1, 9:1, 10:1, 11:1, 12:1, 13:1, 14:1, 15:1, 20:1, 50:1, or 100:1, or any ratio in this range. It will be appreciated however that other ratios may be selected where appropriate.

It will be appreciated that in general aerosolized payload will be introduced into the partially enclosed central space via the lower opening as part of a generated airflow from the blower, pump, fan or pressurized air source of the aerosol generator 230 through a corresponding outlet 218 of the base 200'. Once in the partially enclosed central space, the aerosolized payload cannot easily escape from the lower opening whilst the receptacle 301 remains on the base 200'. However, when the receptacle is picked up, inertia may cause a small proportion of the air and hence also aerosolized payload within the partially enclosed central space to flow out of the lower opening. The relatively small area of the opening can be selected to reduce this effect.

Referring now also to FIGS. 7A-7D, alternatively or in addition a one-way valve may be introduced into the lower opening so that the aerosolized payload can be introduced into the receptacle, but cannot exit via the lower opening. Such a valve may be constructed for example from transparent plastic so as to maintain an overall appearance of the receptacle being made from glass, if this is the chosen material.

Figure 7A:
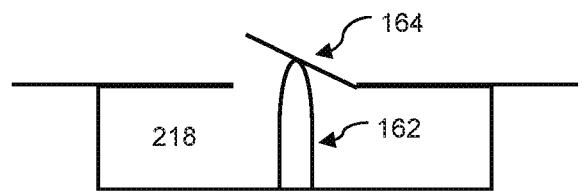
FIGS. 7A-D are schematic diagrams of valve arrangements for an opening in a receptacle of an AP system in accordance with an embodiment of the present disclosure.

FIG. 7A illustrates the outlet 218 in the region between the atomizer 145' and the lower opening 318 of FIG. 6. In this figure, a pin or other protrusion 162 is arranged to extend from the base so as to push up a biased flap 164 covering the lower opening, thereby allowing aerosolized payload into the receptacle while the receptacle is resting on the base. The biased flap returns to the closed position when no longer pushed by the pin or protrusion, and may for example be made from a transparent elastomeric or plastic material.

Figure 7B:
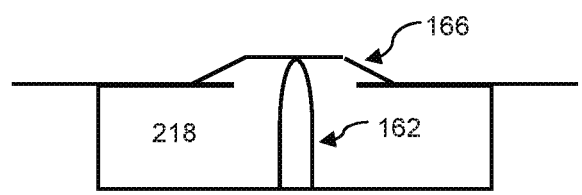
Figure 7C:
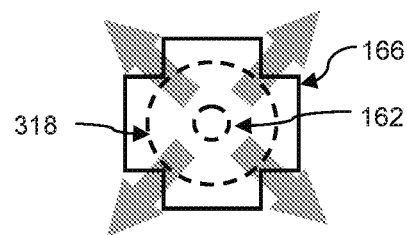

FIGS. 7B and 7C illustrate the same outlet region in both side and plan view to show a similar arrangement with an 'X' shaped elastomeric valve arranged to create a more even distribution of vents into the receptacle through the lower opening so that the aerosolized payload enters the receptacle in a more visually pleasing manner.

Figure 7D:
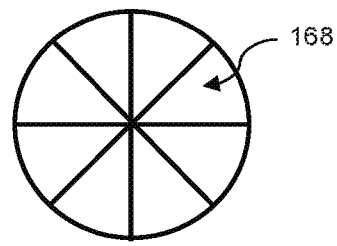

FIG. 7D illustrates an alternative valve for use in the outlet region, comprising (for example) a circular sheet of plastic, silicone or other elastomeric material, or any suitable material, that has had one or more slits cut across a portion of its width, so that the pin or protrusion can pass through the slit or confluence of slits when the receptacle is placed on the base. It will be appreciated that an equivalent arrangement can be generated by the alignment of two or more flaps of suitable material in an adjacent or overlapping manner.

However, it will be appreciated that any suitable valve arrangement may be considered within the scope of the disclosure. Furthermore, it will be appreciated that with the provision of a valve, the absolute or relative size of the lower opening is not important with respect to allowing aerosolized payload to escape from the receptacle and so no specific size or particular ratio with respect to the upper opening need be considered, provided that an appropriate valve is in place.

Referring back to FIG. 6, the base 200' may comprise a sensor 150') substantially similar to that described in relation to FIGS. 1 and 3. The sensor detects when the receptacle is resting on the base and/or when the receptacle is removed from the base. Depending on the nature of the sensor, this may be located so as to be obscured by a suitable receptacle in the case of a light-sensitive sensor, or to be depressed by the receptacle, as in the case of push switch or touch sensitive sensor. It will be appreciated that where the receptacle has a valve, then the pin or protrusion 162 illustrated in FIGS. 7A-C may serve a dual role of opening a valve in the receptacle and detecting that the receptacle is resting on the base, for example through placement of a pressure switch or push switch at the base of the pin or protrusion.

In this way, the control unit in the base can detect when the receptacle is suitably in place to receive a bolus of aerosolized payload from the aerosol generator 145' located in the base.

As with the embodiments illustrated by FIGS. 1 and 3, optionally the base may comprise lighting, such as one or more warm white LEDs to provide a tea light or candle-like effect. Again, the lighting may vary when vapor is being generated in a manner similar to that described previously herein.

It will be appreciated that the arrangement of components illustrated in the base of FIG. 6 is purely illustrative and non-limiting, and that any suitable arrangement may be considered, such as for example the pump, fan or blower being located downstream of the atomizer and arranged to draw air through the atomizer rather than blow air through the atomizer.

Hence for example, referring to FIG. 8 an alternative embodiment may take a form of a base 200" comprising a receptacle, receiver or socket 210 for receiving a typical e-cigarette device 400 or other suitable AP system that comprises its own battery 442, air intake vents 422, heater 446 and liquid reservoir 448. The base still comprises a pump, fan or blower 144, and this is arranged to draw air through the e-cigarette in a manner similar to an inhalation by a user, powered by the base battery 242 or an external power source. The e-cigarette responds to the generated air flow in a normal fashion, detecting a pressure drop due to airflow and activating its heater to create liquid vapor, which mixes with the airflow to create an aerosol. This is drawn through the pump, fan or blower and, if necessary, through a flow guide 136 to an opening in the base corresponding to the lower opening in the receptacle 300. Thus the e-cigarette 400 and the pump, blower or fan 144 co-operate to function in a similar manner to the aerosol generator of preceding embodiments.

The control unit, battery 242, any sensors 150, any valve opening mechanism 162, and any lights referred to previously in relation to the base of FIG. 6 may be included in the base of FIG. 8. Again, the control unit may provide periodic activations of the e-cigarette, and/or in response to the receptacle 301 being placed on the base 200".

In this arrangement, a user can insert a compatible conventional e-cigarette into the base, thereby easily converting the e-cigarette into a multi-user, sociable device. Advantageously, the user will typically have existing familiarity with the operation of the e-cigarette (or other suitable AP system, as appropriate) and can therefore easily perform functions such as changing liquid reservoirs and the like without having to re-familiarize themselves with a new piece of equipment. Furthermore, in a social environment other users can take turns to plug their own compatible AP system into the base, thereby enabling easy sharing of different vapors in a hygienic manner.

Figure 9:
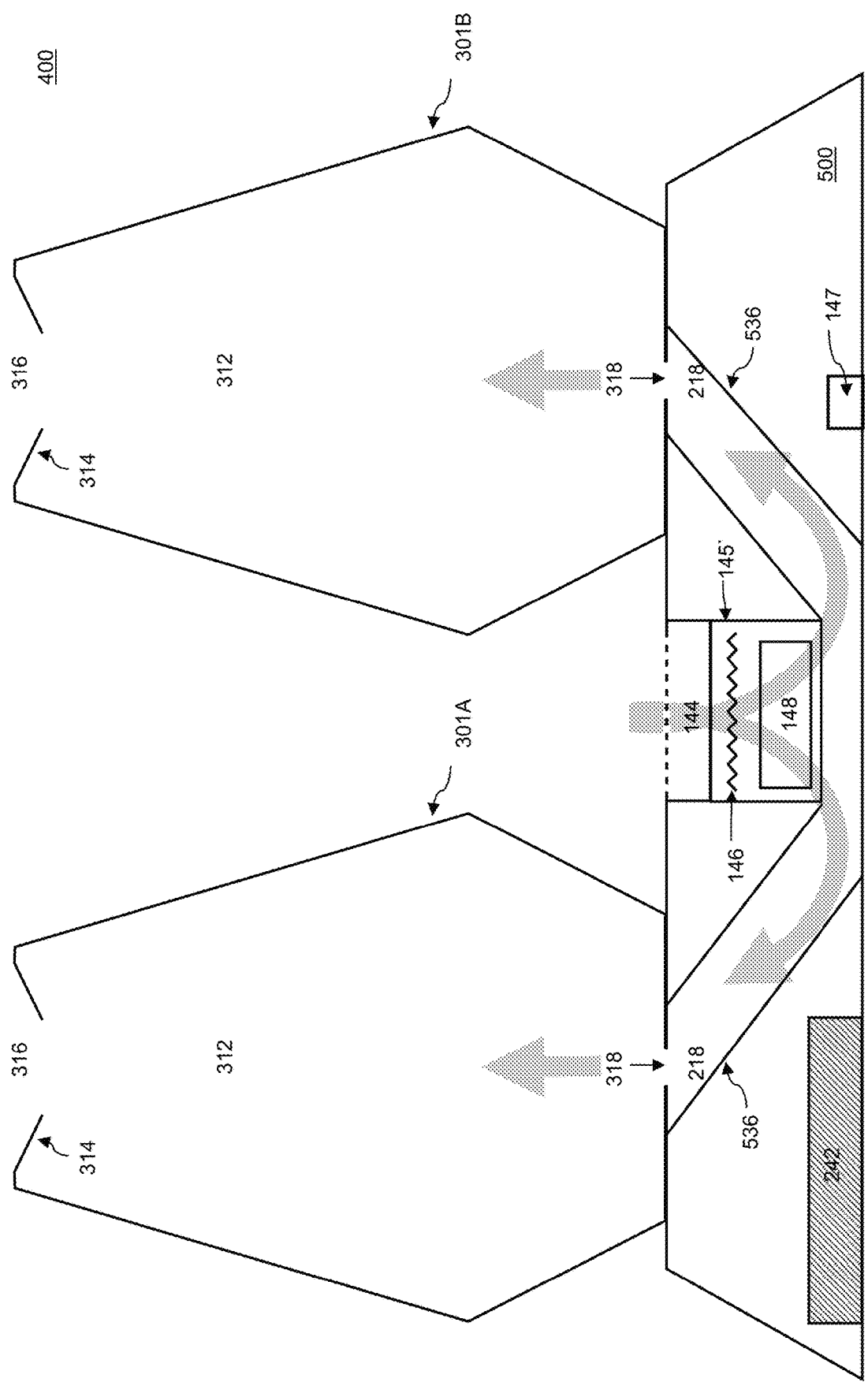
FIG. 9 is a schematic diagram of an AP system in accordance with an embodiment of the present disclosure.

Turning now to FIG. 9, a multi-receptacle AP system 400 may be provided by adapting the base of FIG. 6 or FIG. 8 or any suitable equivalent to form a base 500 operable to provide vapor to more than one receptacle. For example, two, three, four, five or six receptacles (or more) may be received by base having a tray with a corresponding number of placement spaces, where these spaces may typically comprise a recess corresponding in shape to a base part of the receptacles 301.

For simplicity, FIG. 9 illustrates a base for two receptacles 301A, 301B. Notably, the aerosol generator does not need to be located directly beneath either receptacle, and so the aerosol generator can be arranged for example to draw air in through the top of the base using the blower, pump or fan 144 to generate an airflow over the atomizer 145, which in turn generates vapor to mix with the air flow to generate an aerosol in a similar manner to the previous embodiments. However in the present embodiment, the base 500 is operable to channel aerosolized payload to more than one receptacle along suitably formed airflow guides 536, or simply via some or all or a hollow portion of the base body.

As in the embodiments of FIG. 8 and FIG. 6, the control unit, battery 242, any sensors 150, any valve opening mechanism 162, and any lights referred to previously in relation to these figures may be included in the base of FIG. 9. Again, the control unit may provide periodic activations of the aerosol generator, and/or in response to a receptacle 301A,B being placed on the base 500.

Optionally, each placement space or 'docking port' may have its own sensor 150 to detect when a respective receptacle is placed on it. In this case, the control unit may provide individual control of vapor into a receptacle, either by provision of an electronically controlled valve inside the base to limit vapor flow to the placement space (in conjunction with a pin or protrusion opening a valve of the receptacle as noted previously, or simply an opening 318 as noted previously), or by providing electronic control of the pin or protrusion itself to open a valve of the receptacle (for example, by use of a solenoid).

Hence in this instance, aerosolized payload may be allowed into a receptacle when it is placed on the docking port, and then cut-off either after a predetermined period corresponding to an expected time to adequately (re)fill the receptacle, or when the receptacle is removed.

Figure 10:
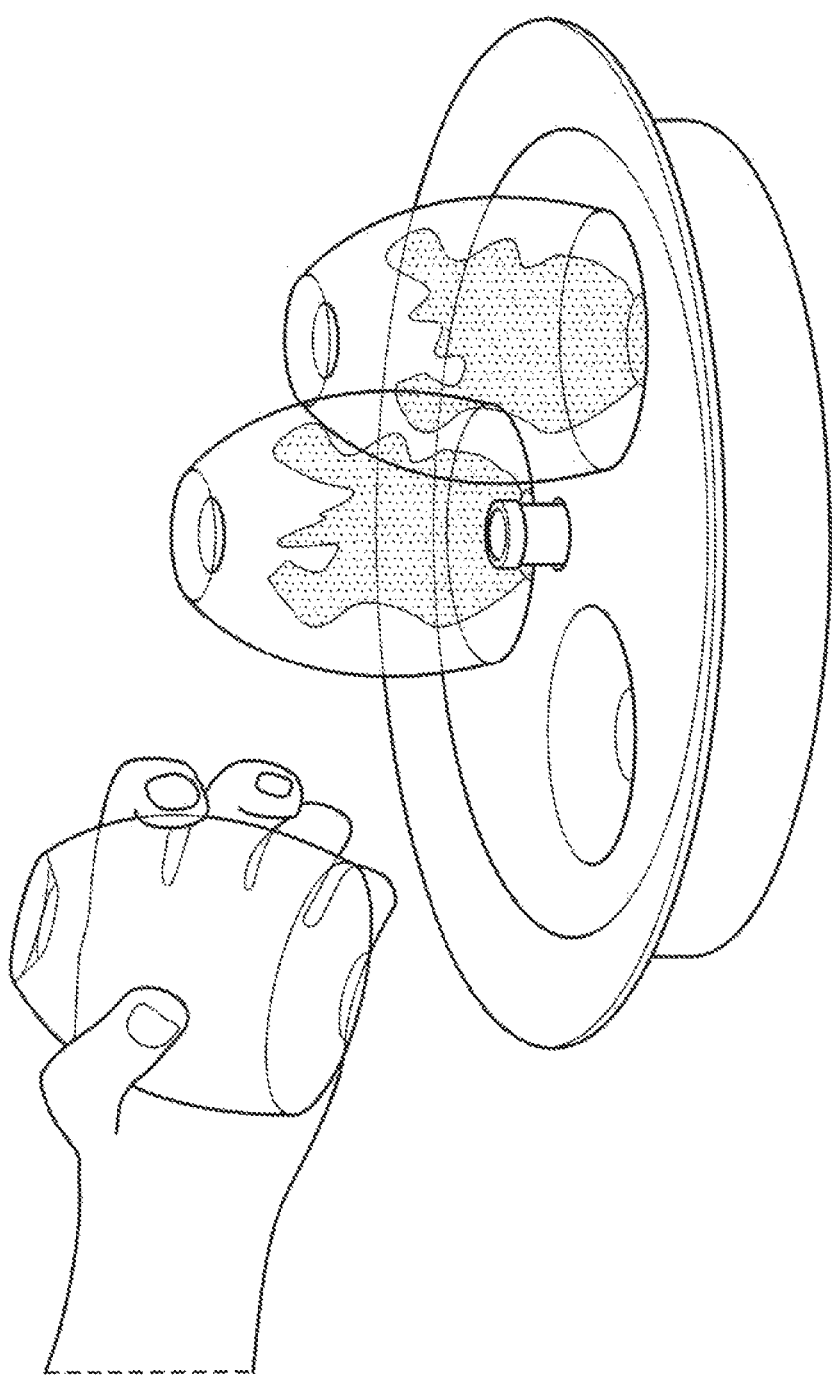
FIG. 10 is an illustrative example of an AP system in accordance with an embodiment of the present disclosure.

An exemplary illustration of the multi-receptacle AP system is provided by FIG. 10.

VARIANT EMBODIMENTS

The above embodiments propose the use of one or more receptacle each having a central volume 112 in which to accumulate an aerosolized payload, in conjunction with an opening 116 from which a user may inhale the aerosolized payload. This allows a user to sample the payload without necessarily touching the receptacle to their lips.

Figure 11:
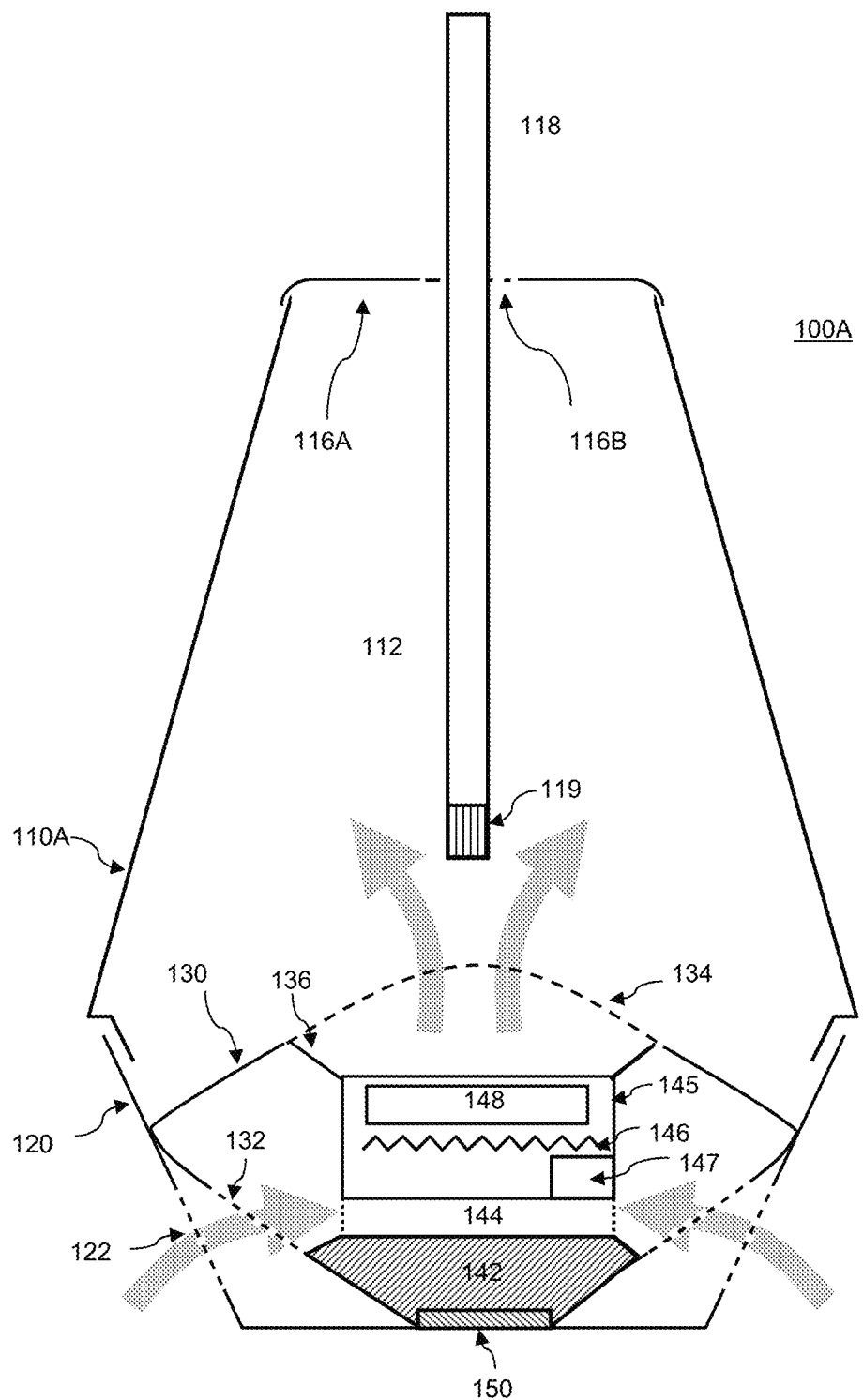
FIG. 11 is a schematic diagram of a variant of the AP system of FIG. 1, in accordance with an embodiment of the present disclosure.
Figure 12:
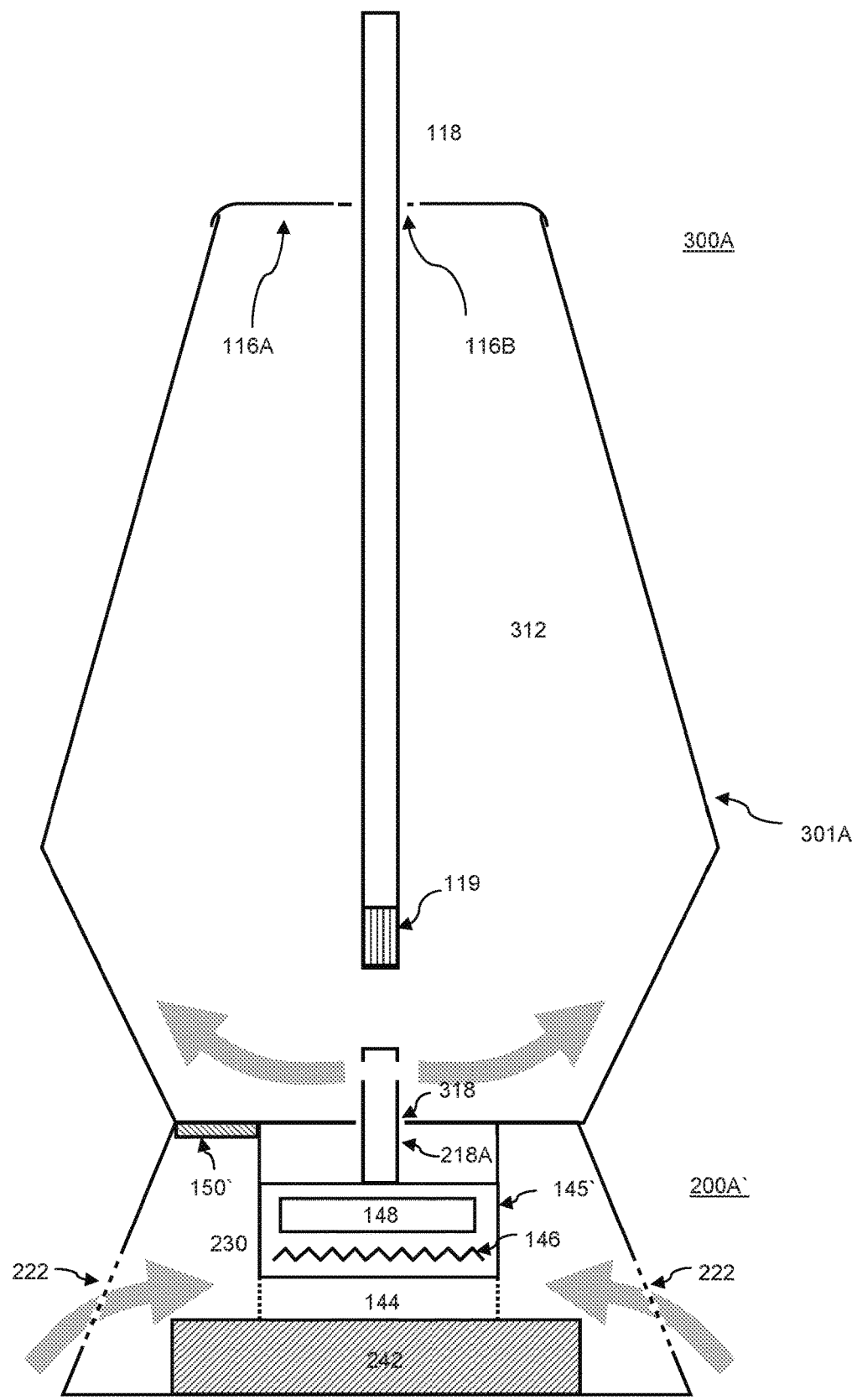
FIG. 12 is a schematic diagram of a variant of the AP system of FIG. 6, in accordance with an embodiment of the present disclosure.

Referring now to FIGS. 11 and 12, these show variants of the embodiments illustrated in FIGS. 1 and 6 and described previously herein. In each case the embodiment is substantially the same as before, except for the modifications described herein below.

In a variant embodiment, the opening lip 114 may optionally be omitted. An (optionally removable) cap 116A is placed over the open top of the receptacle 110A, 301A, and comprises a resealable top valve 116B, which may be similar to valve 164 of FIG. 7A, valve 168 of FIG. 7D or any suitable valve arrangement. The cap itself may comprise an annular seal (not shown) that forms a substantially airtight seal between the cap and the receptacle. The cap may also comprise an adjustable vent (not shown) that may be opened and closed, to allow easy airflow into or out of the receptacle if required.

This cap and valve reduce the rate at which aerosolized payload can escape from the receptacle. This may be desirable so that the user does not feel the need to rush to inhale the contents before they escape, and also potentially to avoid waste if a proportion of the payload escapes before use.

The user then inhales from the receptacle through a straw 118 that is pushed through the top valve 116B. Typically the straw is made of glass or hard transparent plastic, though this is not essential. More generally the straw is rigid and robust when compared, for example, to a conventional drinking straw, but a drinking straw or other disposable straw is envisaged to be within the scope of the disclosure.

Advantageously, the straw mitigates a potential problem with the open topped version of the receptacle; where the user is inhaling the aerosolized payload at the top of the receptacle first, this means that as air enters the top of the receptacle to replace the inhaled payload, it serves to dilute the payload being drawn up by the user; the result is that it is necessary to inhale a much larger volume of air than that originally within the receptacle itself in order to inhale the aerosolized payload in the receptacle. Similarly, successive 'sips' at the open topped receptacle can appear to be successively diluted if the payload is not topped up in between.

By contrast, the straw allows the user to inhale the aerosolized payload from the bottom of the receptacle first. Consequently, air drawn into the top of the receptacle either through the valve or the optional vent during inhalation has a much smaller impact on the concentration of payload near the bottom of the straw. As a result, the user can draw up a significant proportion of the payload without it being diluted, and without needing to inhale additional quantities of air. Typically the straw will have a similar diameter to a cigarette or e-cigarette mouthpiece, for example in the order of 4 mm-10 mm. As a result, the user may expect a similar draw resistance (airflow resistance) to that experienced with a conventional cigarette or e-cigarette. Consequently, an optional flow limiter 119 may be fitted to one end of the straw. The limiter may comprise narrow channels, wadding or baffles to reduce the effective cross sectional area of the straw, thereby providing a similar flow resistance to a conventional cigarette or e-cigarette. Alternatively, an end of the straw may have a lip or constriction in a similar manner to a pipette that similarly acts as a flow limiter. It will be appreciated that optionally the diameter of the straw may approximate the diameter of a conventional cigarette and hence may be in the order of 8 mm to 6 mm in diameter.

In a variant embodiment of the present disclosure specifically relating to the system comprising a base in which the aerosolized payload is generated and then introduced into a receptacle (as shown in FIG. 12), the outlet of the base 218A is arranged to extend above a supporting surface of the base upon which the receptacle is placed, so that it passes through the lower inlet valve by a predetermined amount, typically in the range 0.5 to 4 cm, for example in the range 1 to 3 cm, or for example in the range 1 to 2 cm. Optionally the outlet comprises one or more sideways facing apertures (i.e. facing towards the wall of the receptacle) so that the aerosolized payload is directed substantially horizontally into the receptacle (or, put differently, substantially orthogonal to a direction of flow from the inlet valve to the top valve). The exact angle is not critical, and so the payload may optionally be directed slightly downwards, or slightly upwards. It will be appreciated that an aperture in an outlet with relatively thin walls will have a limited ability to actively guide the flow of payload passing through it, beyond causing the flow to be predominantly on the axis of the aperture at the aperture. Nevertheless, this arrangement encourages the aerosolized payload to fill the receptacle from the bottom up by substantially redirecting the flow horizontally instead of vertically, with reference to the main axis of the receptacle between the inlet and top valves being vertical.

Whilst FIG. 12 shows a base for a single receptacle, it will be appreciated that the variant embodiment can be applied to a base with outlets for 2, 3, 4 or more receptacles, as illustrated previously in FIG. 9.

Figure 13:
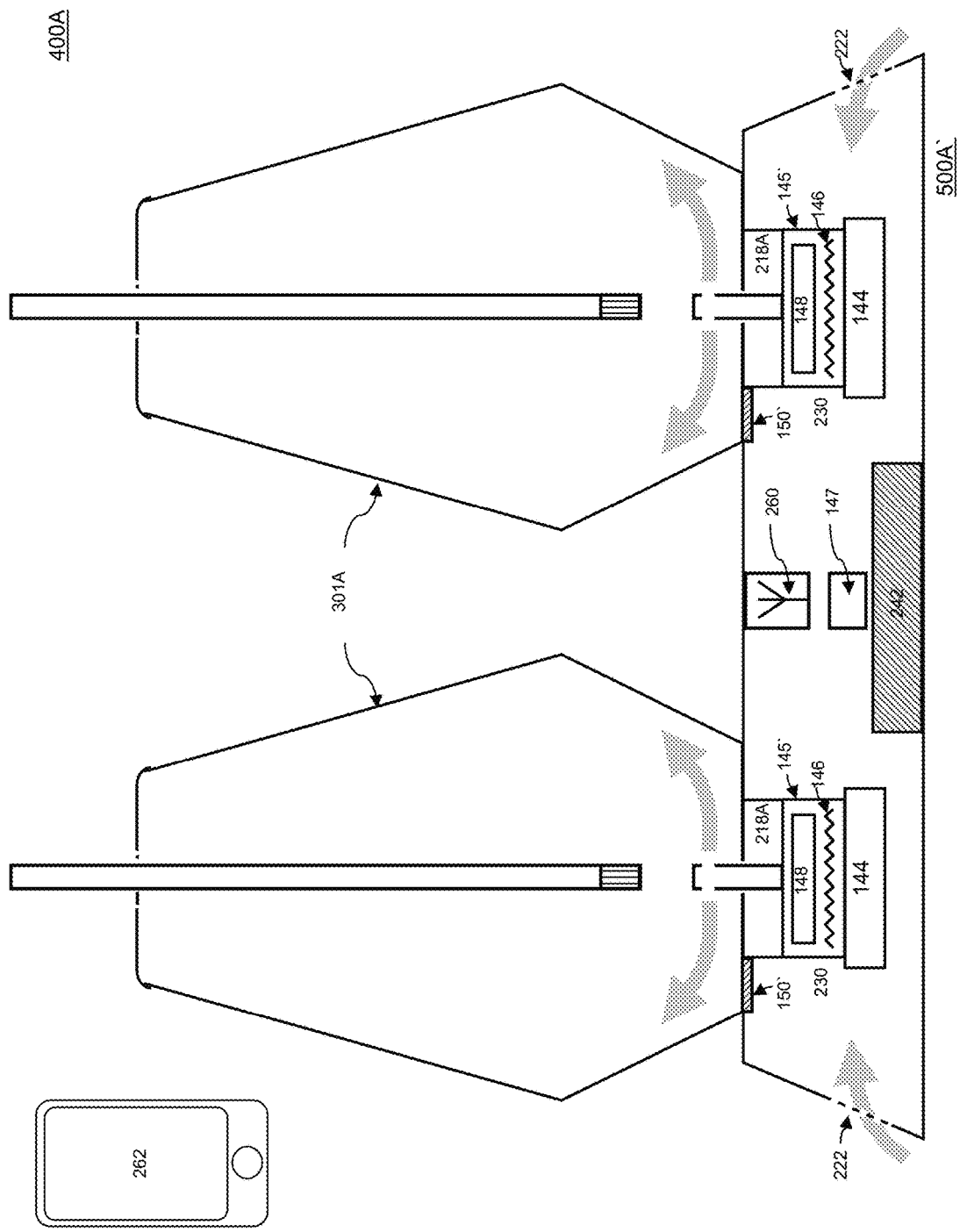
FIG. 13 is a schematic diagram of a variant of the AP system of FIG. 9, in accordance with an embodiment of the present disclosure.

Whilst FIG. 9 shows a single atomizer 230 whose output is distributed to plural receptacles, it will be appreciated that a separate atomizer can be provided for each receptacle such that in FIG. 13 there are N atomizers for N receptacles in a single base. In this case, optionally the N atomizers may share a power source, such as a battery and/or external power supply. It will be appreciated that any combination of atomizer and receptacle may be envisaged; hence for example one atomizer can service all of the receptacles, a plural subset of the receptacles, or a single receptacle. Hence for example a base that services four receptacles may comprise one atomizer for all of the receptacles, or a first atomizer for three receptacles and a second atomizer for one receptacle, or a first atomizer for two receptacles and a second atomizer for two receptacles or alternatively second and third atomizer is for respective receptacles, or four atomizers for four receptacles. Other combinations for different sized bases can be envisaged by the skilled person.

Such a system 400A is illustrated in FIG. 13, which purely for the purposes of clarity shows a base that supports two receptacles, but serves to illustrate embodiments of the base that supports any number of receptacles.

It will be appreciated that, much like the system shown in FIG. 9, the air intake vent or vents may be in any appropriate part of the base, including the top, the side, and underneath (in this case, typically with a plurality of feet being provided on the base to create a gap under the base through which air can pass), and any ducting (if necessary) to guide air to the atomizers may be provided (not shown in FIG. 13).

Respective atomizers in the system 400A can be loaded with different payloads.

In a variant embodiment of the present disclosure, a base supporting N receptacles comprises N removable plates (not shown) upon each of which a receptacle may be placed. Each plate comprises a central aperture through which a respective outlet passes, so that when the receptacle is placed on the plate the outlet also passes through the lower valve of the receptacle. Beneath each plate is a respective atomizer as described previously.

Hence to load an atomizer with a respective payload, the respective plate is removed to reveal the atomizer and payload 148, such as a removable reservoir. The reservoir may screw into a receptacle in the atomizer, such that the number of screw turns terminates with an aperture of the reservoir aligned with an aperture in the atomizer, to allow the flow of payload from the reservoir into the atomizer. The aperture in the reservoir may be coincident with a main axis of the reservoir (e.g. at one end), or orthogonal to it (e.g. on one side). As an alternative to screwing the reservoir into the receptacle, the reservoir may clip into the receptacle. To ensure good alignment between the aperture of the reservoir and the aperture of the atomizer, the reservoir may have a non-symmetrical feature that prevents the reservoir being inserted into the receptacle in any orientation other than the one that results in alignment between the apertures. Optionally the act of pushing or screwing the reservoir into the receptacle may serve to break a seal of the reservoir, thereby allowing the payload to flow out once the reservoir is substantially in place.

In a variant embodiment of the present disclosure, the sensor 150 is a pressure sensor calibrated so as to not be triggered by the presence of the removable plate above it, and optionally calibrated so as not to be triggered by the presence of the receptacle on top of the plate; in this case, the user must therefore tap or press on top of the receptacle (or an accessible portion of the plate) to provide sufficient extra pressure to trigger the sensor. This allows the receptacles to reside on the base without being filled up with aerosolized payload until the user wishes. In one version, the user maintains pressure on the receptacle to control how long payload is introduced into the receptacle, with an optional cut off timer being employed if pressure is exerted for more than a predetermined period of time (for example a predetermined period of time in the range 1-20 seconds, or in the range 3-10 seconds, or for approximately 5 seconds). Alternatively in another version, a tap with sufficient pressure is enough to trigger the atomizing function for a predetermined period of time deemed sufficient to fill the receptacle. This period of time will vary depending on the atomizer and hence may be in the range 1-20 seconds, for example in the range 3-10 seconds, or for approximately 5 seconds.

It will be appreciated that the sensor 150 need not be a pressure sensor but may for example be a capacitance sensor that detects user touch electronically.

Optionally, a light is provided beneath each plate in the base (for example, an LED) lights up when the sensor is activated to indicate that atomizing is taking place. This is to reassure the user that they have pressed both in the correct place and (in the case of a pressure sensor) sufficiently firmly to start the process, even if aerosolized payload is not immediately visible within the receptacle; and indeed in the case that an aerosolized payload is substantially invisible, such a light may provide a useful indication of when the atomizing process starts and ends. Optionally, each light beneath each plate may be of a different color, to make it easier for users to recognize/remember which flavor payload is supplied by a given plate on the device. In this case further optionally the light may be on at a low level continuously so that each plate as a unique appearance, and the light increases in brightness or employs a flashing duty cycle during the atomizing process.

To provide further clarity, the base may have a display indicating what flavor payload is included in what atomizer, and/or an app may be provided that illustrates the base and identifies the flavors associated with each plate (for example by indicating each plate using a color corresponding to a colored light of beneath the plate, and then associating descriptive text with each color, either through a pictorial representation of the device or simply based on color alone. Information identifying the flavor payload may be entered as free text by a user or selected from a drop-down menu or the like for each atomizer of the base.

In a summary embodiment of the present disclosure, an aerosol provision (AP) system 300A, 400A comprises one or more receptacles 301A each forming a respective central space 312; a base 200A', 500A' adapted to support the or each receptacle, the or each receptacle being removable from the base; and a at least a first airflow generator 144, operable to draw air through a at least a first aerosol generator 145'; wherein the base comprises one or more outlets 218A through which, in operation, aerosolized payload is directed to flow from the base through a lower opening 318 of a respective receptacle into the respective central space of said receptacle; and the or each receptacle comprises a top opening that comprises a top valve 116B, through which a user may inhale the aerosolized payload with a straw 118, in one embodiment without needing to touch the receptacle with their lips.

In an instance of this summary embodiment, the base comprises a respective aerosol generator 145' operable to generate said aerosolized payload for each of the or each respective receptacle supported by the base. Hence as described previously herein, one aerosol generator may supply one or more receptacles via respective outlets, and a plurality of aerosol generators may be provided to supply all the supported receptacle is in the chosen configuration. Example configurations include N generators for N receptacles, one generator for N receptacles, one generator for M receptacles where M<N, together with (N–M) generators individually supplying the remaining receptacles, and so on. In this instance, in use the airflow generator 144 can draw air in though a region of the base and through the or each aerosol generator.

An instance of this summary embodiment, the top valve is mounted in a cap 116A that is removably affixed to the top of a respective receptacle. In this case, optionally the cap comprises an adjustable vent operable to be opened or closed to selectively allow air through the cap. As noted previously, this increases displacement airflow and hence can improve the charging or discharging of the central region with aerosolized payload.

In an instance of this summary embodiment, the straw is arranged to have a length that causes the inserted straw to reach a lower portion of the receptacle during normal use. In this case, 'lower portion' can be understood to mean the bottom half of the receptacle, or alternatively can be understood to mean that the straw can touch the inside base of the receptacle whilst still having a working length of the straw protruding from the top valve. However it will be appreciated that unlike a drink, it is not necessary for the straw to reach the bottom of the receptacle in order to access the full content of the receptacle, and indeed it may be advantageous for the straw to be unable to interact with the protruding outlet, as this creates a risk of breakage of either the outlet or the straw. Hence in this case, optionally the straw comprises a stopper (for example a bulge) preventing more than a predetermined length of the straw to pass through the top valve, so that the base of the straw cannot reach the top of the outlet 218A. It will be appreciated that the exact length the straw and the clearance between the base of the straw and the outlet are themselves dependent upon the size and style of the receptacle.

In an instance of this summary embodiment, the straw 118 comprises an airflow restrictor 119. As described above, this serves to increase the flow resistance through the straw to make the effort required to inhale through the straw similar to that required to inhale through a cigarette or e-cigarette.

In an instance of this summary embodiment, a control unit (not shown) issues a signal to the aerosol generator in response to one or more selected from the list consisting of: the elapse of a predetermined period of time (i.e. to periodically recharge the central space with aerosolized payload); the detection of a receptacle being placed on the base (i.e. to refill the receptacle with aerosolized payload when it is placed back on the base); and the detection of pressure exceeding that of a receptacle resting on the base (i.e. to refill the receptacle with aerosolized payload when the user taps or presses on the receptacle, thereby providing additional weight/pressure over and above that of the receptacle itself).

In a summary embodiment of the present disclosure, a hand-held receptacle 301A for holding aerosolized payload comprises a central volume 312, a first upper opening that comprises a top valve 116B through from which an aerosol is inhaled with a straw 118, and a second, lower opening 318 through which the aerosol may be introduced into the central volume.

In an instance of this summary embodiment, the second, lower opening comprises an inlet valve 164, 166.

In an instance of this summary embodiment, the top valve is mounted in a cap 116A that is removably affixed to the top of the hand-held receptacle.

In a summary embodiment of the present disclosure, a base unit 200A', 500A' for an aerosol provision system comprises a support for a plurality of receptacles, each receptacle being removable from the base, a plurality of aerosol generators each operable to generate an aerosolized payload for a respective one of the receptacles, and at least a first airflow generator, operable to draw air through the aerosol generators, wherein the base comprises one or more outlets 218A through which, in operation, respective aerosolized payloads are directed to flow from the base into the respective central space of the or each supported receptacle.

In an instance of this summary embodiment, a system comprises a base unit according to the summary embodiment, and a mobile communication device such as a mobile phone or tablet. The base unit comprises a transmitter adapted to at least one of wired or wirelessly transmit status data of the or each aerosol generator. The status data may comprise one or more selected from the list consisting of: the power status of an aerosol generator (e.g. whether powered on, or more specifically whether currently heating), the payload status of an aerosol generator (e.g. whether a payload reservoir is installed, the flavour/type, of payload, and/or the amount left in the reservoir), whether a receptacle is currently detected as placed on the base in a position corresponding to the respective aerosol generator, whether the aerosol generator is currently, supplying aerosolised payload to a receptacle (e.g. due to the airflow generator and the heater both being in operation), the charge status of a battery power supply if provided, and any potential warning statuses such as a low-power warning, and overheating warning, an empty reservoir warning, a leakage warning (for example if a reservoir is detected as not being properly inserted), and so on. The mobile communication device is adapted to receive the transmitted status data and to display some or all of the status data on a screen of the mobile communication device. For example it may provide a pictographic representation of the base in order to associate status data with respective aerosol generators/receptacle positions of the base. When the base can use differently coloured LEDs for each receptacle position, then a colour coding scheme may be used to associate status data on the display of the mobile device with respective aerosol diameters/receptacle positions of the base.

Referring now to FIG. 14, in another summary embodiment of the present disclosure, a method of aerosol provision comprises:

in s111, providing one or more receptacles 301A each forming a respective central space 312, the or each receptacle having a first opening comprising a valve 116B through which a user may inhale an aerosolized payload with a straw 118, in one embodiment without touching the receptacle with their lips;

in s112, providing a base 200A', 500A' adapted to support the or each receptacle, the or each receptacle being removable from the base;

in s113, providing a plurality of respective aerosol generators 145' operable to generate said aerosolized payload for at least a respective one of the receptacles;

in s114, providing at least a first airflow generator 144, operable to draw air through the aerosol generators 145'; and in 115, directing aerosolized payloads to flow from the base through a lower opening of a respective receptacle into the respective central space of the or each supported receptacle through respective outlets 218A of the base.

It will be apparent to a person skilled in the art that variations in the above method corresponding to operation of the various embodiments of the apparatus as described and claimed herein are also considered within the scope of the present disclosure.

Further variant embodiments include the following:

Multiple flavors provided by the base unit—It will be appreciated that the base need not be restricted to a single aerosol generator supplying aerosolized payload to a plurality of receptacles, but instead two or more aerosol generators may be provided. In this case, different aerosol generators may be loaded with different liquid reservoirs and hence provide different flavors, strengths or other variations of aerosolized payload. Hence for example in the case of a base with four receivers for receptacles, there may be a single aerosol generator supplying all four receptacles, or two aerosol generators each supplying two receptacles, or four aerosol generators each supplying a respective receptacle, and in the case of two or four aerosol generators, then potentially different payloads may be used. In this way a user could load their receptacle with a different flavored vapor by choosing a different receiver, or indeed create a blend of different flavors by placing their receptacle on more than one receiver. It will be appreciated that in principle this approach could also be employed within the receptacle as per FIG. 1 or 11, if the aerosol generators were of a sufficiently small size to allow the accommodation of two or more.

Payload carousel—Again in order to provide multiple flavors from the same base unit, an aerosol generator may be adapted to accommodate a carousel holding two or more payload reservoirs, for example in a carousel for a rotatable selection or a magazine for linear selection; the carousel or magazine can be rotated/shifted to position a particular reservoir in the path of the aerosol generator in order to create a particular flavor of aerosol. The comparatively large size of the base makes accommodation of such a carousel or magazine easy, and a simple mechanical interface to move the carousel or magazine can be provided through the housing of the base (or equally controls for a motorized movement). It will be appreciated that this approach could also be employed where the aerosol generator is incorporated within the receptacle as per FIG. 1 or 11.

Flavor inserts—Within the airflow channel (either before or after generating the aerosol) the cool or hot air, or the aerosolized payload, may pass through or over a flavored substance so that the flavored substance imparts some of its flavor to the aerosolized payload.

For the convenience of the user in terms of adding or removing such an insert, the flavor insert could for example be positioned in the base of the receptacle where the aerosolized payload enters, or within a straw being used to inhale the vapor (potentially also acting as an airflow restrictor to create a draw resistance similar to a traditional cigarette), or more generally at some point on the air flow path, and in one embodiment between the location where the aerosol is formed and the user's mouth.

For example an alternative insert may take the form of an air permeable capsule that fits within the midpoint of the receptacle (for example where the receptacle comes in two parts, the capsule may fit between those two parts in interlocking manner) so that the aerosolized payload must pass through the capsule before being inhaled. Another alternative may be a cylindrical plug that attaches to the lid of the receptacle, and through which the aerosolized payload is inhaled via the straw. A further alternative may be to provide a single use or limited use receptacle with a gel, oil or other flavored substance coated or otherwise adhered to at least part of the inside surface of the receptacle or to specific structures such as fins, grilles or other shapes for example having a relatively large surface area that are included near the base of the receptacle in the flow path the aerosol as it is introduced into the receptacle. A further alternative may be to provide a single use or limited use straw with a gel, oil or other flavored substance coated on at least part of the internal surface of the straw.

An example of the flavored substance itself could be a tobacco plug, for example loose leaf tobacco contained in a porous container, which imparts a tobacco flavor to the aerosol. More generally the flavored substance could be in any form, such as a single body such as a gel or tobacco plug, or smaller, loose parts such as loose leaf tobacco freely movable within an air-permeable container.

It will be appreciated that the above concepts may be combined, for example so that flavor inserts may be mounted in a carousel so that the different flavors can be easily introduced into the air/aerosol flow path. It will similarly be appreciated that different flavor insert could be provided by using different straws either comprising an air/aerosol permeable plug or an inner coating, as discussed above.

Multiple supplies to a docking port—Referring back to FIG. 9 by way of example, an aerosol generator can supply a plurality of receptacles via appropriate ducting and a respective outlet 218 at the docking port of the receptacle. By contrast referring to FIG. 13, it will be appreciated that a plurality of aerosol generators can be housed within the base, each supplying a respective outlet 218A.

Combining these features in this variant embodiment, a base may comprise a plurality of aerosol generators, each of which is operably coupled to appropriate ducting to supply aerosolized payload to a plurality of receptacles. These may remain separate (for example, as mentioned previously herein two aerosol generators may respectively and separately supply two docking ports of a four-receptacle system), but alternatively they may be arranged to both supply one or more receptacles via a docking port, for example through multiple outlets 218, 218A. Alternatively, the mixing of aerosols may occur prior to flowing into a single outlet (for example, having an inverted 'Y' outlet receiving two aerosol flows, with a valve on at least one of the flows to control its introduction into a mix).

Hence (and using specific flavors purely as a non-limiting example) a first aerosol generator may supply a cherry flavored vapor to a receptacle via a first outlet in a docking port, whilst a second aerosol generator may supply a strawberry flavored vapor to the same receptacle via a second outlet in the same docking port, thereby providing a mix of flavors.

Optionally actuation of an outlet may be selective, so that the user may select between strawberry or cherry or both. Selection may be via a mechanical restriction of the airflow or operation/disabling of a release valve, or by pressing the appropriate button related to allowing electrical actuation of one or both release valves. It will also be appreciated that in addition to simply variants of flavor, different types of payload could be mixed in this way; for example, an aerosol generated by heating tobacco (without combustion) could be blended with an aerosol generated by vaporizing an e-liquid or a similar liquid or gel.

Whilst it will be appreciated that the base unit may readily accommodate multiple aerosol generators in this manner, it will be appreciated that in much the same way as was noted for the multiple flavors discussed previously herein, in principle this approach could also be employed within the receptacle as per FIG. 1 or 11, if the aerosol generators were of a sufficiently small size to allow the accommodation of two or more. Hence difference flavors and/or aerosols generated from different payload types (e.g. heated tobacco and a liquid) could be supplied in parallel by aerosol generators within a receptacle.

Receptacle with nozzle—Referring again to FIGS. 11, 12 and 13, as an alternative to having a cap 116A comprising an opening for a straw, the cap may comprise an integral nozzle, spout or similar mouthpiece which the user places within their mouth to inhale the aerosolized payload found within the receptacle. The receptacle may thus have a similar mode of operation to a so-called non-spill cup or sippy cup'. The cap or lid may be removable or integral to the receptacle (for example in the case of single use or limited use receptacles). The mouthpiece can be formed as a protrusion within the surface of the cap or lid. Alternatively, the open top of the receptacle could narrow to a sufficiently small radius that the tip of the receptacle itself can be placed within the user's mouth and acts as a nozzle directly. In this case the radius may be in the range 2 cm down to 1 mm, for example in the range 1.5 cm down to 2 mm, or for example in the range 1 cm down to 3 mm, or for example in the range 9 mm down to 4 mm, and or for example in the range 8 mm to 6 mm.

Squeezable receptacle—Previously herein the receptacle is referred to as being glass or plastic. It will be appreciated that the receptacle could use a deformable plastic (such as Polyethelene Terephthalate) with sufficiently thin walls to be a squeezable container. Subsequently the user may squeeze the receptacle to force or squirt the aerosolized payload into their mouth, either through an upper opening in the receptacle, or through a straw or nozzle depending on the embodiment. It will be appreciated that in this case the receptacle will comprise a valve at the lower opening, for example such as one of the valves shown in FIGS. 7A-D, which prevents or limits aerosolized payload from escaping through the lower opening of the receptacle when it is being squeezed.

Inflatable receptacle—In a similar manner to the squeezable receptacle, the receptacle could be made from an elastomeric material such as rubber or latex so that it is inflatable like a balloon. In this case, the balloon may have only a single opening and be placed over an outlet of the base, thereby being inflated with aerosolized payload to an extent determined by the output pressure of the airflow generator and the length of time during which aerosol is applied to the inflatable receptacle. The user may then remove the receptacle and either squeeze it or let it naturally deflate in order to force the aerosolized payload into their mouth. Alternatively, the receptacle may resemble receptacles discussed previously herein in relation to the base as illustrated for example in FIGS. 9 and 13, having an upper opening or straw and a lower input valve, but comprise an elastomeric portion that can inflate when an aerosolized payload is introduced. In this case, the upper opening or straw may have a removable cap that serves to allow a buildup of pressure within the receptacle until the cap is removed/released, enabling the elastomeric material to deflate and force vapor into the user's mouth.

Hydra receptacle—In this variant embodiment, a base supplies a receptacle that comprises a plurality of inhalation vents (e.g. upper openings, nozzles and/or top valves 116B for straws 118. This enables a plurality of users to simultaneously inhale the aerosolized payload within the receptacle. To accommodate this variant use, potentially the receptacle is larger than the hand-held receptacles described previously, thereby holding a larger volume of aerosolized payload and also facilitating simultaneous access in close proximity by several users.

For example, the receptacle may be a glass or plastic dome or bell that can be placed over the top of the base. The base may be arranged to accommodate the dome (for example having an annular ring of silicone, and/or a circumferential trench, to receive the dome with a substantially airtight fit). The base may be arranged specifically to supply a dome, or may be similar to the base units described previously. In this latter case the dome may be used conventionally for individual hand held receptacles as described previously herein, and also in a mode where one or more of the outlets in the base is activated to supply vapor within the dome. This may be done using an electrical activation of an outlet, or by a mechanical linkage to an outlet, such as an extension of one or more pressure plates described previously herein to a position where the dome rests on the base. An equivalent variant for the receptacle of FIGS. 1 and 11 is to enlarge the receptacle, for example to form a spherical or ovoid bowl with a diameter between 10 and 30 cm, or example between 15 and 25 cm, or for example approximately 20 cm. The precise shape of the bowl as not essential and can be selected for aesthetic reasons. The aerosol generator resides within the bowl as described previously herein and supplies vapor.

It will be appreciated that any suitable combinations from these variant embodiments and previously described embodiments may be envisaged within the scope of the disclosure. For example, multiple flavors may be supplied to a hydra receptacle, or different flavor inserts may be used at respective inhalation points on a hydra receptacle. Meanwhile the receptacle of FIG. 1 or 11 may use a nozzle instead of an opening or a valve for a straw, and some or all of the receptacle may be squeezable. Other combinations will be apparent to the skilled person.

Finally, embodiments may incorporate subject matter of the following numbered clauses:

Clause 1. An aerosol provision (AP) system, comprising:
one or more receptacles each forming a respective partially enclosed central space;
a base adapted to support the or each receptacle, the or each receptacle being removable from the base; and
an airflow generator, operable to draw air through an aerosol generator;
wherein
the base comprises one or more outlets through which, in operation, aerosolized payload is directed to flow from the base into the respective partially enclosed central space of the or each supported receptacle; and
the or each receptacle comprises a first opening from which a user may inhale the aerosolized payload, without needing to touch the receptacle with their lips.

Clause 2. An AP system according to clause 1, wherein the base comprises:

an aerosol generator operable to generate said aerosolized payload.

Clause 3. An AP system according to clause 2, in which in use the airflow generator draws air in though a region of the upper surface of the base and through the aerosol generator.

Clause 4. An AP system according to any one of clauses 2 or 3, comprising:
a control unit arranged to activate the airflow generator without a corresponding activation of an atomizer of the aerosol generator.

Clause 5. An AP system according to clause 1, wherein the base comprises:
a receiver arranged to receive a separate AP system comprising an aerosol generator, the separate AP system being operable to generate aerosolized payload in response to air being drawn through the separate AP system by the airflow generator of the base.

Clause 6. An AP system according to any one of the preceding clauses, in which
the or each receptacle comprises a second, lower opening having an area smaller than the first opening; and
the aerosolized payload is arranged to flow from the base into the respective partially enclosed central space of the or each supported receptacle through said second lower opening.

Clause 7. An AP system according to clause 6, in which the second lower opening is restricted by an inlet valve to prevent aerosolized payload from flowing out of the second lower opening when the receptacle is removed from the base.

Clause 8. An AP system according to clause 7, in which the base comprises one or more valve actuators each operable to open a corresponding respective inlet valve of a receptacle when it is supported by the base.

Clause 9. An AP system according to clause 8, in which
the base comprises a control unit; and
the valve actuator selectively opens the respective inlet valve in response to a signal from the control unit.

Clause 10. An AP system according to clause 9, in which
the control unit issues a signal to the valve actuator in response to one or more selected from the list consisting of:
i. the elapse of a predetermined period of time; and
ii. the detection of a receptacle being placed on the base.

Clause 11. An AP system according to any one of the preceding claims in which the first opening comprises a lip that curves down towards the partially enclosed central space.

Clause 12. A hand-held receptacle for holding aerosolized payload, comprising:
a partially enclosed central volume;
a first upper opening from which an aerosol may be inhaled; and
a second, lower opening through which the aerosol may be introduced into the partially enclosed central volume; in which
the first upper opening is larger than the second lower opening.

Clause 13. The hand-held receptacle of clause 12, in which the second, lower opening comprises an inlet valve.

Clause 14. The hand-held receptacle of clause 12 or clause 13, in which the upper opening has a lip that curves down towards the partially enclosed central space.

Clause 15. A base unit for an aerosol provision system, comprising:

a support for one or more receptacles, the or each receptacle being removable from the base; and an airflow generator, operable to draw air through an aerosol generator;

wherein the base comprises one or more outlets through which, in operation, aerosolized payload is directed to flow from the base into the respective partially enclosed central space of the or each supported receptacle.

Clause 16. A base unit according to clause 15 wherein the base comprises:

an aerosol generator operable to generate said aerosolized payload.

Clause 17. A base unit according to clause 16, in which in use the airflow generator draws air in though a region of the upper surface of the base and through the aerosol generator.

Clause 18. A base unit according to clause 16 or 17, comprising:

a control unit arranged to activate the airflow generator without a corresponding activation of an atomizer of the aerosol generator.

Clause 19. A base unit according to clause 15 wherein the base comprises:

a receiver arranged to receive a separate AP system comprising an aerosol generator, the separate AP system being operable to generate aerosolized payload in response to air being drawn through the separate AP system by the airflow generator of the base.

Clause 20. A method of aerosol provision comprising:

providing one or more receptacles each forming a respective partially enclosed central space, the or each receptacle comprising a first opening from which a user may inhale an aerosolized payload, without touching the receptacle with their lips;

providing a base adapted to support the or each receptacle, the or each receptacle being removable from the base;

providing an airflow generator, operable to draw air through an aerosol generator; and directing aerosolized payload to flow from the base into the respective partially enclosed central space of the or each supported receptacle through one or more respective outlets of the base.

Clause 21. A method according to clause 20, wherein the base comprises an aerosol generator operable to generate said aerosolized payload.

Clause 22 A method according to clause 21, comprising:

activating the aerosol generator without a corresponding activation of a heater of the aerosol generator.

Clause 23. A method according to clause 20, comprising.

receiving at the base a separate AP system comprising an aerosol generator, the separate AP system being operable to generate aerosolized payload in response to air being drawn through the separate AP system by the airflow generator of the base.

Clause 24. A method according to any one of clauses 20 to 22, in which the or each receptacle comprises a second, lower opening having an area smaller than the first opening, the method comprising:

directing the aerosolized payload to flow from the base into the respective partially enclosed central space of the or each supported receptacle through said second lower opening.

Clause 25. A method according to clause 23, comprising:

restricting the flow of aerosolized payload out of the second lower opening when the receptacle is removed from the base.

Clause 26. A method according to clause 24, comprising:

selectively opening the second lower opening in response to one or more selected from the list consisting of:

i. the elapse of a predetermined period of time; and ii. the detection of a receptacle being placed on the base.

The invention claimed is:

1. An aerosol provision (AP) system, comprising:

one or more receptacles each forming a respective central space and having a lower opening;

at least one aerosol generator;

a base adapted to support the one or more receptacles, the one or more receptacles being removable from the base;

at least a first airflow generator of the base operable to draw air through at least a first aerosol generator, the base comprising or receiving the first aerosol generator; and wherein the base comprises or receives a payload comprising an aerosol material configured to be aerosolized and the base comprises one or more outlets through which, in operation, the aerosolized payload is directed to flow from the base, through the lower opening, into the central space of a respective receptacle of the one or more receptacles, and the one or more receptacles comprises a first opening through which the user can inhale the aerosolized payload.

2. The AP system according to claim 1, wherein the first opening comprises a top valve through which a user inhales the aerosolized payload with a straw.

3. The AP system according to claim 2, wherein in use the airflow generator draws air in though a region of the base and through the aerosol generator.

4. The AP system according to claim 2, wherein the top valve is mounted in a cap that is removably affixed to a respective one of the one or more receptacles over the first opening of a respective one of the one or more receptacles.

5. The AP system according to claim 4, wherein the cap comprises an adjustable vent operable to be opened or closed to selectively allow air through the cap.

6. The AP system according to claim 2, wherein the straw is arranged to have a length that causes the straw, when inserted, to reach a lower portion of the receptacle during normal use.

7. The AP system according to claim 2, wherein the straw comprises a flavor insert comprising a flavored material in the form of one of a permeable plug, a gel, or an inner coating.

8. The AP system according to claim 2, wherein the straw comprises an airflow restrictor.

9. The AP system according to claim 1, wherein the base comprises:

the at least first aerosol generator operable to supply the aerosolized payload to the one or more outlets.

10. The AP system according to claim 1, wherein the base comprises:

a plurality of aerosol generators, including the at least first aerosol generator, each operable to supply a respective aerosolized payload to a respective one of the one or more outlets.

11. The AP system according to claim 1, wherein the base comprises:

a plurality of aerosols generators operable to simultaneously supply a respective aerosolized payload to the same outlet of the one or more outlets.

12. The AP system according to claim 1, wherein a second opening in the one or more receptacles for allowing aerosolized payload into the central space is restricted by an inlet valve to prevent aerosolized payload from flowing out of the second opening when the one or more receptacles are removed from the base.

13. The AP system according to claim 1, wherein the one or more receptacles comprise a plurality of openings through which the aerosolized payload is able to be inhaled.

14. The AP system according to claim 1, further comprising:
a control unit of the base configured to issue a signal to the aerosol generator in response to one or more conditions selected from the group consisting of:
elapse of a predetermined period of time;
detection of a receptacle being placed on the base; and
detection of pressure exceeding that of a receptacle resting on the base.

15. A hand-held receptacle for holding aerosolized payload, the receptacle resembling a tumbler or drinking glass, comprising:
structure defining a central volume;
structure defining a first upper opening that comprises a top valve through which an aerosol is inhaled with a straw; and
structure defining a second lower opening comprising an inlet valve through which the aerosol is introduced into the partially enclosed central volume,
wherein the top valve is mounted in a cap that is removably affixed to a top of the hand-held receptacle.

16. The hand-held receptacle according to claim 15, wherein the hand-held receptacle comprises one or more additional upper openings.

17. A base unit for an aerosol provision system, comprising:
a supporting surface of the base unit upon which a plurality of receptacles are positionable, each of the plurality of receptacles being removable from the supporting surface;
one or more payloads comprising aerosol material;
one or more aerosol generators each operable to generate an aerosolized payload for one or more of the plurality of receptacles; and
at least a first airflow generator operable to draw air through the one or more aerosol generators;
wherein the base unit comprises one or more outlets in the supporting surface through which, in operation, respective aerosolized payloads are directed to flow from the base unit into a central space of one of the plurality of supported receptacles, wherein an aerosolized payload is directed to flow from the base, through a lower opening, into the central space of a respective receptacle of the one or more receptacles.

18. The base unit for an aerosol provision system according to claim 17, wherein the one or more aerosol generators are arranged to generate the aerosolized payload for each respective one of the plurality of receptacles.

19. A system comprising:
the base unit according to claim 17; and
a mobile communication device;
wherein the base unit comprises a transmitter adapted to at least one of wired or wirelessly transmit status data of the one or more aerosol generators, and the mobile communication device is adapted to receive the transmitted status data and to display some or all of the status data on a screen of the mobile communication device.

20. A method of aerosol provision system comprising:
providing one or more receptacles each forming a respective central space and having a lower opening, the one or more receptacles each having an opening through which a user can inhale an aerosolized payload without touching the receptacle with their lips;
providing a base adapted to support the one or more receptacles, the one or more receptacles being removable from the base;
providing in the base a plurality of respective aerosol generators operable to generate the aerosolized payload for at least a respective one of the one or more receptacles;
providing in the base at least an airflow generator operable to draw air through the plurality of aerosol generators;
providing one or more payloads comprising aerosol material in the base; and
directing respective aerosolized payloads to flow from the base, through the lower opening, into the respective central space of the one or more supported receptacles, through respective outlets of the base.

* * * * *